(12) United States Patent
Winslow et al.

(10) Patent No.: US 12,383,494 B2
(45) Date of Patent: Aug. 12, 2025

(54) PACKAGING FOR RAPIDLY INFUSING COMPOSITION

(71) Applicant: ORCOSA INC., Ewing, NJ (US)

(72) Inventors: Simon Winslow, Ewing, NJ (US); Vincent T. Mileto, Flemington, NJ (US)

(73) Assignee: ORCOSA, INC., Ewing, NJ (US)

( * ) Notice: Subject to any disclaimer, the term of this patent is extended or adjusted under 35 U.S.C. 154(b) by 185 days.

(21) Appl. No.: 18/252,674

(22) PCT Filed: Nov. 4, 2021

(86) PCT No.: PCT/US2021/058045
§ 371 (c)(1),
(2) Date: May 11, 2023

(87) PCT Pub. No.: WO2022/103648
PCT Pub. Date: May 19, 2022

(65) Prior Publication Data
US 2024/0009129 A1   Jan. 11, 2024

Related U.S. Application Data

(63) Continuation of application No. 17/225,738, filed on Apr. 8, 2021, now Pat. No. 11,672,761.
(Continued)

(51) Int. Cl.
*A61J 1/03* (2023.01)
*A61K 9/00* (2006.01)
(Continued)

(52) U.S. Cl.
CPC ............ *A61K 9/006* (2013.01); *A61K 9/0053* (2013.01); *A61K 9/08* (2013.01); *A61K 9/145* (2013.01);
(Continued)

(58) Field of Classification Search
CPC ........... A61J 1/035; A61J 1/03; B65D 75/327; B65D 75/36; B65D 75/367; B65D 75/325;
(Continued)

(56) References Cited

U.S. PATENT DOCUMENTS 3,894,896 A * 7/1975 Watanabe ............... B29C 51/14
156/212
5,110,007 A * 5/1992 Law ................... B65D 83/0463
221/25
(Continued)

FOREIGN PATENT DOCUMENTS

AU        2019379706 A1    6/2021
CN          1320887 C      6/2007
(Continued)

OTHER PUBLICATIONS

International Search Report and Written Opinion issued Jan. 28, 2022 in PCT/US21/58045 filed Nov. 4, 2021, 5 pages.
(Continued)

*Primary Examiner* — Steven A. Reynolds
(74) *Attorney, Agent, or Firm* — Patterson + Sheridan, LLP

(57) ABSTRACT

A container for a lyophilized rapidly infusing composition is described. The container comprises a planar lidding layer attached to a well layer comprising pockets for the therapeutic product. The lidding layer may comprise an aluminum layer, a thermoplastic polymer layer, and a labeling layer. The well layer may comprise an aluminum layer, two polyamide layers, and two thermoplastic polymer layers. A drug product assembly is also disclosed, which includes at least one therapeutic product sealed within the at least one pocket of the container.

31 Claims, 6 Drawing Sheets

Related U.S. Application Data

(60) Provisional application No. 63/180,193, filed on Apr. 27, 2021, provisional application No. 63/172,343, filed on Apr. 8, 2021, provisional application No. 63/172,386, filed on Apr. 8, 2021, provisional application No. 63/172,362, filed on Apr. 8, 2021, provisional application No. 63/172,368, filed on Apr. 8, 2021, provisional application No. 63/147,453, filed on Feb. 9, 2021, provisional application No. 63/114,194, filed on Nov. 16, 2020, provisional application No. 63/114,181, filed on Nov. 16, 2020.

(51) Int. Cl.
| | | |
|---|---|---|
| *A61K 9/08* | (2006.01) | |
| *A61K 9/14* | (2006.01) | |
| *A61K 9/19* | (2006.01) | |
| *A61K 9/20* | (2006.01) | |
| *A61K 31/00* | (2006.01) | |
| *A61K 31/05* | (2006.01) | |
| *A61K 31/4045* | (2006.01) | |
| *A61K 31/465* | (2006.01) | |
| *A61K 31/496* | (2006.01) | |
| *A61K 31/519* | (2006.01) | |
| *A61K 31/592* | (2006.01) | |
| *A61K 31/593* | (2006.01) | |
| *A61K 45/06* | (2006.01) | |
| *A61K 47/10* | (2017.01) | |
| *A61K 47/26* | (2006.01) | |
| *A61K 47/42* | (2017.01) | |
| *A61K 47/46* | (2006.01) | |
| *A61P 23/00* | (2006.01) | |
| *A61P 25/08* | (2006.01) | |
| *A61P 25/16* | (2006.01) | |

(52) U.S. Cl.
CPC ............... *A61K 9/146* (2013.01); *A61K 9/19* (2013.01); *A61K 9/2063* (2013.01); *A61K 31/05* (2013.01); *A61K 31/4045* (2013.01); *A61K 31/465* (2013.01); *A61K 31/496* (2013.01); *A61K 31/519* (2013.01); *A61K 31/592* (2013.01); *A61K 31/593* (2013.01); *A61K 31/658* (2023.05); *A61K 45/06* (2013.01); *A61K 47/10* (2013.01); *A61K 47/26* (2013.01); *A61K 47/42* (2013.01); *A61K 47/46* (2013.01); *A61P 23/00* (2018.01); *A61P 25/08* (2018.01); *A61P 25/16* (2018.01)

(58) Field of Classification Search
CPC .............. B65D 75/326; B65D 83/0463; B65D 2075/365; B65D 2075/362; B65D 2075/363; B65D 75/32; B65D 75/366; B65D 75/34
USPC ................................ 206/531, 534, 538, 528
See application file for complete search history.

(56) References Cited

U.S. PATENT DOCUMENTS

| | | | | |
|---|---|---|---|---|
| 5,112,616 | A | | 5/1992 | McCarty |
| 5,343,672 | A | * | 9/1994 | Kearney ............... B65D 75/327 53/343 |
| 5,457,895 | A | * | 10/1995 | Thompson ........... A61K 9/2095 34/296 |
| 5,631,023 | A | | 5/1997 | Kearney et al. |
| 5,720,974 | A | | 2/1998 | Makino et al. |
| 5,729,958 | A | | 3/1998 | Kearney et al. |
| 6,007,824 | A | | 12/1999 | Duckett et al. |
| 6,307,346 | B1 | | 10/2001 | Downer et al. |
| 6,316,027 | B1 | | 11/2001 | Johnson et al. |
| 6,316,029 | B1 | | 11/2001 | Jain et al. |
| 6,391,237 | B1 | | 5/2002 | Kearney et al. |
| 6,509,040 | B1 | | 1/2003 | Murray et al. |
| 6,534,094 | B2 | | 3/2003 | Moyano et al. |
| 6,709,669 | B1 | | 3/2004 | Murray et al. |
| 6,830,153 | B2 | * | 12/2004 | French ................ B65D 75/327 206/538 |
| 6,860,405 | B1 | | 3/2005 | Poynter |
| 7,090,866 | B2 | | 8/2006 | Johnson et al. |
| 7,135,180 | B2 | | 11/2006 | Truong-Le |
| 7,331,460 | B2 | | 2/2008 | Barndt et al. |
| 7,360,652 | B2 | | 4/2008 | Arnold |
| 7,393,674 | B2 | | 7/2008 | Jiang et al. |
| 7,395,928 | B2 | * | 7/2008 | Bertsch ................ B65D 75/327 206/532 |
| 7,464,818 | B2 | | 12/2008 | Gherdan et al. |
| 7,607,834 | B2 | | 10/2009 | Alvater et al. |
| 7,758,936 | B2 | * | 7/2010 | Spallek ................ B32B 27/304 428/34.1 |
| 7,771,745 | B2 | | 8/2010 | Wang et al. |
| 7,799,860 | B2 | | 9/2010 | Sugishita et al. |
| 7,951,397 | B2 | | 5/2011 | Dietrich et al. |
| 7,968,594 | B2 | | 6/2011 | Guy et al. |
| 7,972,621 | B2 | | 7/2011 | Wong et al. |
| 8,268,354 | B2 | | 9/2012 | Truong-Le et al. |
| 8,445,524 | B2 | | 5/2013 | Courvoisier et al. |
| 8,545,836 | B2 | | 10/2013 | Kaul et al. |
| 8,545,879 | B2 | | 10/2013 | Burns et al. |
| 8,598,207 | B2 | | 12/2013 | Buehler |
| 8,647,668 | B2 | | 2/2014 | Tanaka et al. |
| 8,722,366 | B2 | | 5/2014 | Sasaki et al. |
| 8,802,145 | B2 | | 8/2014 | Bauer |
| 8,865,722 | B2 | | 10/2014 | Hrakovsky et al. |
| 8,946,153 | B2 | | 2/2015 | Gupta et al. |
| 8,974,824 | B2 | | 3/2015 | Amminabavi et al. |
| 9,066,870 | B2 | | 6/2015 | Hu et al. |
| 9,119,794 | B2 | | 9/2015 | Middlbeek et al. |
| 9,241,902 | B2 | | 1/2016 | Rowe et al. |
| 9,265,764 | B2 | | 2/2016 | Haggarty et al. |
| 9,408,879 | B2 | | 8/2016 | Guglielmetti et al. |
| 9,415,015 | B2 | | 8/2016 | Jacobi et al. |
| 9,468,679 | B2 | | 10/2016 | Debunne et al. |
| 9,492,379 | B2 | | 11/2016 | Park et al. |
| 9,629,920 | B2 | | 4/2017 | Leighton et al. |
| 9,717,681 | B2 | | 8/2017 | Banbury et al. |
| 9,717,684 | B2 | | 8/2017 | Bhavsar et al. |
| 9,717,692 | B2 | | 8/2017 | Bilgic |
| 9,731,018 | B2 | | 8/2017 | Ahuja et al. |
| 9,775,819 | B2 | | 10/2017 | Bahl et al. |
| 9,808,521 | B2 | | 11/2017 | Weigandt et al. |
| 9,820,937 | B2 | | 11/2017 | Brewer et al. |
| 9,833,408 | B1 | | 12/2017 | Greenspoon |
| 9,839,613 | B2 | | 12/2017 | Qiao et al. |
| 9,872,873 | B2 | | 1/2018 | Khattar et al. |
| 9,895,342 | B2 | | 2/2018 | Maione et al. |
| 9,901,603 | B2 | | 2/2018 | Borody |
| 9,956,169 | B2 | | 5/2018 | Tian et al. |
| 9,963,265 | B1 | * | 5/2018 | Braverman ........ B65D 21/0206 |
| 9,974,826 | B2 | | 5/2018 | Klein et al. |
| 9,980,915 | B2 | | 5/2018 | Matsuoka et al. |
| 10,064,849 | B2 | | 9/2018 | Ridall et al. |
| 10,086,078 | B2 | | 10/2018 | Ahuja et al. |
| 10,137,167 | B2 | | 11/2018 | Klein et al. |
| 10,226,525 | B2 | | 3/2019 | Anderson et al. |
| 10,307,394 | B2 | | 6/2019 | Chistov |
| 10,307,397 | B2 | | 6/2019 | Allen et al. |
| 10,307,459 | B2 | | 6/2019 | Nilsson et al. |
| 10,383,911 | B2 | | 8/2019 | Abels et al. |
| 10,420,809 | B2 | | 9/2019 | Crowley |
| 10,548,839 | B2 | | 2/2020 | Tian |
| 10,604,467 | B2 | | 3/2020 | Emanuele et al. |
| 10,617,650 | B2 | | 4/2020 | Bhambhani et al. |
| 10,624,940 | B2 | | 4/2020 | Speier |
| 10,632,164 | B2 | | 4/2020 | Schaneville |
| 10,695,332 | B2 | | 6/2020 | Ridall et al. |
| 10,799,467 | B2 | | 10/2020 | Whalley et al. |
| 10,888,518 | B2 | | 1/2021 | Jaspart et al. |
| 10,888,519 | B2 | | 1/2021 | Soni et al. |

(56) References Cited

U.S. PATENT DOCUMENTS

| | | | |
|---|---|---|---|
| 10,905,681 B2 | 2/2021 | Wrobel et al. | |
| 10,925,853 B2 | 2/2021 | Bruun et al. | |
| 10,928,829 B2 | 2/2021 | Tatourian et al. | |
| 10,973,766 B2 | 4/2021 | Pillay et al. | |
| 10,988,638 B2 | 4/2021 | Wong et al. | |
| 11,000,480 B2 | 5/2021 | Deshpande et al. | |
| 12,043,463 B1 * | 7/2024 | Braverman | B65D 77/2056 |
| D1,062,448 S * | 2/2025 | Washington | D28/4 |
| 2003/0017209 A1 | 1/2003 | Parikh et al. | |
| 2003/0229027 A1 | 12/2003 | Eissens et al. | |
| 2004/0023948 A1 | 2/2004 | Green et al. | |
| 2004/0076666 A1 | 4/2004 | Green et al. | |
| 2004/0156894 A1 | 8/2004 | Grother et al. | |
| 2005/0042177 A1 | 2/2005 | Ryde et al. | |
| 2006/0093679 A1 | 5/2006 | Mayer et al. | |
| 2006/0134195 A1 | 6/2006 | Fu et al. | |
| 2006/0138016 A1 * | 6/2006 | Harper | A61J 1/035 206/532 |
| 2007/0122355 A1 | 5/2007 | Monteith et al. | |
| 2007/0134493 A1 | 6/2007 | Meghpara | |
| 2007/0259857 A1 | 11/2007 | Gray | |
| 2007/0298090 A1 | 12/2007 | Chen et al. | |
| 2008/0200452 A1 | 8/2008 | Obermeier et al. | |
| 2008/0213343 A1 | 9/2008 | Obermeier et al. | |
| 2008/0251411 A1 * | 10/2008 | Walker | B32B 15/08 206/484 |
| 2008/0305168 A1 | 12/2008 | Moon et al. | |
| 2009/0226522 A1 | 9/2009 | Howes et al. | |
| 2009/0308780 A1 * | 12/2009 | Nonomura | A61K 31/4245 206/524.4 |
| 2010/0239646 A1 | 9/2010 | Nair | |
| 2011/0097395 A1 | 4/2011 | Babul et al. | |
| 2011/0217313 A1 | 9/2011 | Becker et al. | |
| 2011/0268809 A1 | 11/2011 | Brinkley et al. | |
| 2012/0118788 A1 * | 5/2012 | Stevens | B65D 75/327 206/531 |
| 2012/0165413 A1 | 6/2012 | Fujiwara et al. | |
| 2013/0015095 A1 * | 1/2013 | Carson | A61J 1/035 206/533 |
| 2013/0039981 A1 | 2/2013 | Cherurkuri | |
| 2014/0079756 A1 | 3/2014 | Andersen et al. | |
| 2015/0096920 A1 * | 4/2015 | Trombley | B65D 75/36 206/531 |
| 2015/0133504 A1 | 5/2015 | Ridall et al. | |
| 2015/0191288 A1 * | 7/2015 | Jolley | A61M 15/0045 206/438 |
| 2016/0015683 A1 | 1/2016 | McCarty | |
| 2016/0058866 A1 | 3/2016 | Sekura et al. | |
| 2016/0159541 A1 | 6/2016 | Brandl | |
| 2016/0243055 A1 | 8/2016 | Yeshurun | |
| 2017/0112762 A1 | 4/2017 | Sivert et al. | |
| 2017/0295817 A1 | 10/2017 | Rojano Jorge et al. | |
| 2017/0319433 A1 * | 11/2017 | Hosoi | B32B 27/20 |
| 2017/0326147 A1 | 11/2017 | Sa et al. | |
| 2017/0348249 A1 | 12/2017 | Negre et al. | |
| 2018/0064645 A1 | 3/2018 | Greenspoon | |
| 2018/0092853 A1 | 4/2018 | Hassan et al. | |
| 2018/0110810 A1 | 4/2018 | Sadowsky et al. | |
| 2018/0153794 A1 | 6/2018 | Coric et al. | |
| 2018/0169022 A1 | 6/2018 | Jaspart et al. | |
| 2018/0279641 A1 | 10/2018 | Dong | |
| 2018/0311205 A1 | 11/2018 | Morgan | |
| 2018/0369221 A1 | 12/2018 | Ridall et al. | |
| 2019/0008848 A1 | 1/2019 | Zhang et al. | |
| 2019/0008870 A1 | 1/2019 | Chen | |
| 2019/0070124 A1 | 3/2019 | Anavi-Goffer | |
| 2019/0083391 A1 | 3/2019 | Bond | |
| 2019/0083611 A1 | 3/2019 | Yi | |
| 2019/0307675 A1 | 10/2019 | Rosenbaum et al. | |
| 2019/0314274 A1 | 10/2019 | Masto et al. | |
| 2019/0314368 A1 | 10/2019 | Liang et al. | |
| 2019/0328673 A1 | 10/2019 | Wan et al. | |
| 2019/0388392 A1 | 12/2019 | Ahmed et al. | |
| 2020/0009232 A1 | 1/2020 | Fuhrherr et al. | |
| 2020/0022945 A1 | 1/2020 | Swartout | |
| 2020/0022993 A1 | 1/2020 | Zhong et al. | |
| 2020/0054563 A1 | 2/2020 | Li et al. | |
| 2020/0061138 A1 | 2/2020 | Williams | |
| 2020/0115317 A1 | 4/2020 | Mechoulam et al. | |
| 2020/0138704 A1 | 5/2020 | Wan et al. | |
| 2020/0138721 A1 | 5/2020 | Grother et al. | |
| 2020/0138730 A1 | 5/2020 | Madwar et al. | |
| 2020/0170933 A1 | 6/2020 | Wong et al. | |
| 2020/0190215 A1 | 6/2020 | Schwaeble et al. | |
| 2020/0197364 A1 | 6/2020 | Prud'Homme et al. | |
| 2020/0222402 A1 | 7/2020 | Purohit et al. | |
| 2020/0222529 A1 | 7/2020 | Zhang | |
| 2020/0237733 A1 | 7/2020 | Geissler et al. | |
| 2020/0253875 A1 | 8/2020 | Coffman et al. | |
| 2020/0268667 A1 | 8/2020 | McLaughlin et al. | |
| 2020/0268668 A1 | 8/2020 | McLaughlin et al. | |
| 2020/0268676 A1 | 8/2020 | McLaughlin et al. | |
| 2020/0268677 A1 | 8/2020 | McLaughlin et al. | |
| 2020/0269546 A1 * | 8/2020 | Fogtmann | B32B 15/12 |
| 2020/0316025 A1 | 10/2020 | Sreedharala et al. | |
| 2020/0330423 A1 | 10/2020 | Brunn et al. | |
| 2020/0330425 A1 | 10/2020 | Bruun et al. | |
| 2020/0368197 A1 | 11/2020 | Donaduzzi et al. | |
| 2020/0383969 A1 | 12/2020 | Coric et al. | |
| 2020/0390704 A1 | 12/2020 | McLaughlin et al. | |
| 2021/0000814 A1 | 1/2021 | Coric et al. | |
| 2021/0008191 A1 | 1/2021 | Conlan et al. | |
| 2021/0267934 A1 | 9/2021 | Macphail et al. | |
| 2022/0151934 A1 | 5/2022 | Ridall et al. | |
| 2024/0082107 A1 * | 3/2024 | Laugros | B65D 75/327 |

FOREIGN PATENT DOCUMENTS

| | | |
|---|---|---|
| EP | 1 171 134 A1 | 1/2002 |
| EP | 1780005 A1 | 5/2007 |
| EP | 1787800 A1 | 5/2007 |
| EP | 2 722 036 A1 | 4/2014 |
| EP | 2 428 202 B1 | 7/2015 |
| EP | 3 479 822 A1 | 5/2019 |
| GB | 1 548 022 | 7/1979 |
| JP | 2017-155049 | 9/2017 |
| WO | WO 00/54777 A1 | 9/2000 |
| WO | WO 2019/042247 A1 | 9/2000 |
| WO | WO 2013/165468 A1 | 11/2013 |
| WO | WO 2016/014454 A1 | 1/2016 |
| WO | WO 2018/082814 A1 | 5/2018 |
| WO | WO 2018/222923 A1 | 12/2018 |
| WO | WO 2019/153064 A1 | 8/2019 |
| WO | WO 2019/219773 A1 | 11/2019 |
| WO | WO 2019/231225 A1 | 12/2019 |
| WO | WO 2019/231865 A1 | 12/2019 |
| WO | WO 2019/232783 A1 | 12/2019 |
| WO | WO 2020/024011 A1 | 2/2020 |
| WO | WO 2020/037152 A1 | 2/2020 |
| WO | WO 2020/051371 A2 | 3/2020 |
| WO | WO 2020/061584 A1 | 3/2020 |
| WO | WO 2020/098774 A1 | 5/2020 |
| WO | WO 2020/121326 A1 | 6/2020 |
| WO | WO 2020/146753 A1 | 7/2020 |
| WO | WO 2020/165407 A1 | 8/2020 |
| WO | WO 2020/171727 A2 | 8/2020 |
| WO | 2020/185214 A1 | 9/2020 |
| WO | WO 2020/186010 A1 | 9/2020 |
| WO | WO 2020/188568 A1 | 9/2020 |

OTHER PUBLICATIONS

International Search Report and Written Opinion issued Jan. 31, 2022 in PCT/US21/58061 filed Nov. 4, 2021, 8 pages.

International Search Report and Written Opinion issued Feb. 4, 2022 in PCT/US21/59184 filed Nov. 12, 2021, 8 pages.

International Search Report and Written Opinion issued Feb. 8, 2022 in PCT/US21/59088 filed Nov. 12, 2021, 12 pages.

International Search Report and Written Opinion issued Feb. 1, 2022 in PCT/US21/57938 filed Nov. 3, 2021, 8 pages.

International Search Report and Written Opinion issued Jan. 31, 2022 in PCT/US21/57901 filed Nov. 3, 2021, 10 pages.

(56) References Cited

OTHER PUBLICATIONS

International Search Report and Written Opinion issued Feb. 10, 2022 in PCT/US21/58038 filed Nov. 4, 2021, 12 pages.
International Search Report and Written Opinion issued Jan. 31, 2022 in PCT/US21/57931 filed Nov. 3, 2021, 8 pages.
International Search Report and Written Opinion issued Feb. 16, 2022 in PCT/US21/57917 filed Nov. 3, 2021, 10 pages.
International Search Report and Written Opinion issued Mar. 10, 2022 in PCT/US21/059140 filed Nov. 12, 2021, 10 pages.
International Search Report and Written Opinion issued Mar. 8, 2022 in PCT/US21/057915 filed Nov. 3, 2021, 12 pages.
Kasteler et al. "Low-dose methotrexate administered weekly is an effective corticosteroid-sparing agent for the treatment of the cutaneous manifestations of dermatomyositis," Journal of the American Academy of Dermatology, vol. 36. Issue 1. (1997) pp. 67-71, [Retrieved on Jan. 10, 2022], Retrieved from <URL:https://sci-hub.se/10.1016/s0190-9622(97)70327-x>.
Baghdadi, "Effect of methotrexate use on the development of type 2 diabetes in rheumatoid arthritis patients: A systematic review and meta-analysis." PLOS One, vol. 15(7):e0235637. Jul. 6, 2020 (Jul. 6, 2020) [Retrieved on Jan. 10, 2022], Retrieved from <URL:https://doi.org/10.1371/journal.pone.0235637>.
"Why Do I Need Folic Acid When I'm Taking Methotrexate?" (Evans) Oct. 8, 2020 (Oct. 8, 2020), [Retrieved on Jan. 10, 2022], Retrieved from <URL:https://www.goodrx.com/methotrexate/why-do-i-need-folic-acid-when-taking- methotrexate>.
"Gelatin vs. Veggie Capsules & CBD" , Millie, Oct. 9, 2020, 4 pages, Retrieved from <URL: https://millie.co/blogs/cbd/gelatin-vs-veggie-capsules-cbd>.
Chandrasekhar et al., "The role of formulation excipients in the development of lyophilised fast-disintegrating tablets", European Journal of Pharmaceutics and Biopharmaceutics, vol. 72 Issue 1 (Dec. 3, 2008): pp. 119-129.
Augusto dos Santos Garcia et al., "Gelatin/starch orally disintegrating films as a promising system for vitamin C delivery", Food Hydrocolloids, vol. 79 (2018): pp. 127-135.
Seager H, "Drug-delivery Products and the Zydis Fast-dissolving Dosage Form", J Pharm Pharmacol, 1998, 50, pp. 375-382.
Damle B et al., "Pharmacokinetics of a Novel Orodispersible Tablet of Sildenafil in Healthy Subjects", Clinical Therapeutics, vol. 36, No. 2, 2014, pp. 236-244.
Zhu et al., "An evaluation of anti-hyperalgesic effects of cannabidiolic acid-methyl ester in a preclinical model of peripheral neuropathic pain", British Journal of Pharmacology, vol. 177, pp. 2712-2725. (Year: 2020).
Lu et al., "An Introduction to the Endogenous Cannabinoid System", Biological Psychiatry, 2016, 36 pages.
Guindon et al., "The endocannabinoid system and pain", CNS Neurol Disord Drug Targets, 2009; 8 (6), 39 pages.
Bergamaschi et al., "Safety and side effects of cannabidiol, a Cannabis sativa constituent", Current Drug Safety, 2011; 6, pp. 237-249.
Iffland et al., "An update on safety and side effects of cannabidiol: a review of clinical data and relevant animal studies", Cannabis and Cannabinoid Research, (2017) 2:1, pp. 139-154.
Zhornitsky et al., "Cannabidiol in humans-the quest for therapeutic targets", Pharmaceuticals, 2012; 5(5), pp. 529-552.
Parker et al., "Regulation of nausea and vomiting by cannabinoids", British Journal of Pharmacology, 2011; 163(7), pp. 1411-1422.
"Tablet," Stedman's Medical Dictionary (1972), 22nd ed, p. 1250.
"Tablet," Stedman's Medical Dictionary (1990), 25th ed, pp. 1549-1550.
"Tablet," Stedman's Medical Dictionary (1995), 26th ed, pp. 1757-1758.
"Tablet," Stedman's Medical Dictionary (2006), 28th ed, pp. 1930-1931.
Hu, S. et al. "A mussel-inspired film for adhesion to wet buccal tissue and efficient buccal drug delivery," Nature Communications, 12:1689 (2021).
Alaia et al., "Buccally Absorbed Cannabidiol Shows Significantly Superior Pain Control and Improved Satisfaction Immediately After Rotator Cuff Repair," The American Journal of Sports Medicine 1-8 (2022).
Notcutt, W. et al., "Initial experiences with medicinal extracts of cannabis for chronic pain: Results from 34 'N of 1' studies," Anaesthesia, 2004, 59, pp. 440-452.
Millar, S.A. et al., "A systematic review of cannabidiol dosing in clinical populations," British Journal of Clinical Pharmacology, 2019, 85, pp. 1888-1900.
Abilify FDA Label, Otsuka Pharmaceutical Co., Ltd., 2014.
Epidiolex FDA label, Greenwich Biosciences, Inc., 2021.
Ward et al., Cannabidiol inhibits paclitaxel-induced neuropathic pain through 5-HT1 Areceptors without diminishing nervous system function of chemotherapy efficacy, Oct. 4, 2013, British Journal of Pharmacology, vol. 171, pp. 636-645. (Year: 2013).
European Search Report dated Oct. 21, 2024 re EP Application No. 21892604.6.

\* cited by examiner

PACKAGING FOR RAPIDLY INFUSING COMPOSITION

CROSS REFERENCE TO RELATED APPLICATIONS

This application claims priority to U.S. patent application Ser. No. 17/225,738 filed Apr. 8, 2021, which claims priority to U.S. Provisional Application No. 63/114,194 filed Nov. 16, 2020; U.S. Provisional Application No. 63/114,181 filed Nov. 16, 2020; U.S. Provisional Application No. 63/147,453 filed Feb. 9, 2021; U.S. Provisional Application No. 63/172,343 filed Apr. 8, 2021; U.S. Provisional Application No. 63/172,362 filed Apr. 8, 2021; U.S. Provisional Application No. 63/172,386 filed Apr. 8, 2021; U.S. Provisional Application No. 63/172,368 filed Apr. 8, 2021; and U.S. Provisional Application No. 63/180,193 filed Apr. 27, 2021; which are each incorporated herein by reference in their entirety.

BACKGROUND OF THE INVENTION

Field of the Invention

The present invention relates to a blister packaging for a lyophilized rapidly infusing composition.

DISCUSSION OF THE BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Blister packaging is commonly used for holding individual units of a pharmaceutical product. Blister packaging typically comprises an aluminum laminate lid layer adhered to a base having a formed blister, generally of transparent plastic. The lid layer and blister are joined to form a sealed cavity within which the product rests. Products, in particular drug products, administered in an orally disintegrating tablet (ODT) are more convenient to use and address potential issues of patient compliance for certain product indications and patient populations. ODT products are designed to disintegrate or dissolve rapidly upon contact with saliva, thus eliminating the need to chew the tablet, swallow an intact tablet, or take the tablet with food or liquid. However, lyophilized orally disintegrating tablets, particularly those with a more rapid disintegration profile, present unique challenges related to heat transfer during the freezing and lyophilization steps, structural integrity of the packaging and the ODT itself, and moisture transmission that can damage the tablet's disintegrating ability or reduce shelf-life. Additionally, active therapeutic ingredients (ATI) within such tablets may be damaged by moisture, oxygen transmission, and light exposure thereby reducing the efficacy of the ODT. This is especially true for orally disintegrating tablets comprising nicotine or cannabidiol.

What is needed to overcome these challenges is a blister packaging having an opaque, metallized, and formable bottom layer of pockets that can be used for holding a suspension in a lyophilization process. The blister packaging as sealed must have low moisture and oxygen transmission rates and must shield completely against light.

SUMMARY OF THE INVENTION

In view of the forgoing, there is a need for a blister packaging for therapeutic products, and specifically for therapeutic products in the form of rapidly infusing compositions.

Accordingly, it is one object of the present disclosure to provide a blister packaging.

It is another object of the present disclosure to provide a drug product container assembly of a blister packaging enclosing a therapeutic product.

It is another object of the present disclosure to provide a drug product container assembly of a blister packaging enclosing a lyophilized rapidly infusing composition that promotes heat transfer during the freezing and lyophilization steps and reduces frost heave caused by the upward swelling of the tablet surface as the unit crystalizes and increases the ice content during the controlled freezing step.

It is another object of the present disclosure to provide a drug product container assembly of a blister packaging enclosing a rapidly infusing composition comprising a pharmaceutically acceptable binder and/or excipient system comprising gelatin and mannitol.

It is another object of the present disclosure to provide a drug product container assembly of a blister packaging enclosing a rapidly infusing composition comprising a therapeutically effective amount of cannabidiol or a derivative/analog thereof.

It is another object of the present disclosure to provide a drug product container assembly of a blister packaging enclosing a rapidly infusing composition comprising nicotine.

It is another object of the present disclosure to provide a drug product container assembly of a blister packaging that is not easily opened by a child.

The present invention provides:

(1) A container for packaging a therapeutic product, comprising:
  a substantially planar lidding layer, and
  a well layer,
  wherein the lidding layer comprises, in order from an exterior lid side to an interior lid side:
  a labeling layer;
  a thermoplastic polymer lidding layer; and
  an aluminum lidding layer;
  wherein interior lid side is removably attached to an interior well side,
  wherein the well layer is shaped to form one or more pockets between the interior lid side and the interior well side, each pocket configured to enclose the therapeutic product, and
  wherein the well layer comprises, in order from the interior well side to an exterior well side:
  a first thermoplastic polymer well layer;
  a first polyamide layer;
  an aluminum well layer;
  a second polyamide layer; and
  a second thermoplastic polymer well layer.

(2) The container of (1), wherein the lidding layer and/or the well layer further comprise adhesive interlayers.

(3) The container of (1) or (2), wherein the lidding layer and the well layer each independently have:
  a moisture vapor transmission rate (MVTR) of less than 0.05 g/m²/day measured at 38° C. and 90% relative humidity, and/or an oxygen transmission rate (OTR) of less than 0.01 m/m$^2$/day measured at 23° C. and 50% relative humidity.

(4) The container of any one of (1) to (3), wherein the lidding layer further comprises a lacquer layer at the interior lid side.

(5) The container of any one of (1) to (4), wherein the thermoplastic polymer lidding layer, the first thermoplastic polymer well layer, and the second thermoplastic polymer well layer each independently comprise at least one polymer selected from the group consisting of polyvinylchloride, polyethylene terephthalate, polyamide, polyethylene, poly (lactic-co-glycolic acid), polytetrafluoroethylene, polyvinylidene fluoride, polylactic acid, polypropylene, polystyrene, polyvinyl acetate, and polyvinylidene chloride.

(6) The container of any one of (1) to (5), wherein the first and second thermoplastic polymer well layers consist essentially of polyvinylchloride.

(7) The container of any one of (1) to (6), wherein the first and second polyamide layers comprise oriented polyamide.

(8) The container of any one of (1) to (7), wherein the labeling layer comprises paper.

(9) The container of any one of (1) to (8), wherein the lidding layer has an average layer thickness in a range of 90-130 μm, and
   wherein the well layer has an average layer thickness in a range of 190-300 μm.

(10) The container of any one of (1) to (9), having one or more edges or corners where the lidding layer and the well layer are not attached to each other.

(11) The container of any one of (1) to (10), wherein the lidding layer and the well layer form at least two pockets, and
   wherein the lidding layer and the well layer have a perforated line between the at least two pockets.

(12) The container of any one of (1) to (11), wherein the lidding layer and the well layer form at least three pockets separated by at least two perforated lines, and wherein each adjacent two perforations are spaced by a distance in a range of 20-50 mm.

(13) The container of any one of (1) to (12), wherein the lidding layer and/or the well layer are knurled where the interior lid side is removably attached to the interior well side of the well layer.

(14) The container of any one of (1) to (13), wherein the one or more pockets are each rotationally symmetric about a central axis and have a non-convex cross-sectional profile.

(15) The container of any one of (1) to (14), wherein the one or more pockets each comprise a substantially flat portion in the center of the pocket.

(16) The container of (15), wherein the substantially flat portion in the center of the pocket includes a raised or lowered portion(s) to deboss or emboss a logo or other information into the therapeutic product.

(17) The container of (15) or (16), wherein the substantially flat portion of the one or more pockets is connected to the top of the pocket by a sidewall comprising two or more sections, wherein a lower section of the sidewall exhibits a greater degree of concavity than an upper section of the sidewall.

(18) The container of any one of (1) to (17), wherein the one or more pockets each has a volume in a range of 0.3-4.0 cm$^3$.

(19) The container of any one of (1) to (18), wherein the one or more pockets each has a vertical depth in a range of 3-10 mm.

(20) The container of any one of (17), wherein the lower section of the sidewall and an upper section of the sidewall each comprises a plurality of planar faces.

(21) The container of any one of (15) to (17), wherein the substantially flat portion in the center of the pocket is an octagonal in shape.

(22) A drug product container assembly, comprising the container of any one of (1) to (21) and at least one therapeutic product in the at least one pocket, wherein the at least one therapeutic product is a rapidly infusing composition.

(23) The drug product container assembly of (22), wherein the rapidly infusing composition is lyophilized and has a disintegration time of approximately 1 to 30 seconds in deionized water maintained at 37° C.±2° C.

(24) The drug product container assembly of (22), wherein the rapidly infusing composition is lyophilized and has a disintegration time of approximately 1 to 5 seconds in deionized water maintained at 37° C.±2° C.

(25) The drug product container assembly of any one of (22) to (24), wherein the rapidly infusing composition comprises a pharmaceutically acceptable binder and/or excipient system comprising gelatin and mannitol.

(26) The drug product container assembly of any one of (22) to (25), wherein the rapidly infusing composition comprises a therapeutically effective amount of cannabidiol or a derivative/analog thereof.

(27) The drug product container assembly of any one of (22) to (26), wherein the rapidly infusing composition comprises a therapeutically effective amount of cannabidiol.

(28) The drug product container assembly of any one of (22) to (27), wherein the rapidly infusing composition comprises a therapeutically effective amount of a derivative/analog of cannabidiol.

(29) The drug product container assembly of (28), wherein the derivative/analog of cannabidiol is cannabidiolic acid methyl ester.

(30) The container of any one of (15) to (21), wherein the substantially flat portion in the center of the pocket comprises a raised portion forming an identifiable feature.

(31) The container of any one of (15) to (21) or (30), wherein the substantially flat portion in the center of the pocket comprises a depressed portion forming an identifiable feature.

BRIEF DESCRIPTION OF THE DRAWINGS

The foregoing paragraphs have been provided by way of general introduction, and are not intended to limit the scope of the following claims. The described embodiments, together with further advantages, will be best understood by reference to the following detailed description when considered in conjunction with the accompanying drawings, wherein.

DETAILED DESCRIPTION OF THE INVENTION

Figure 1:
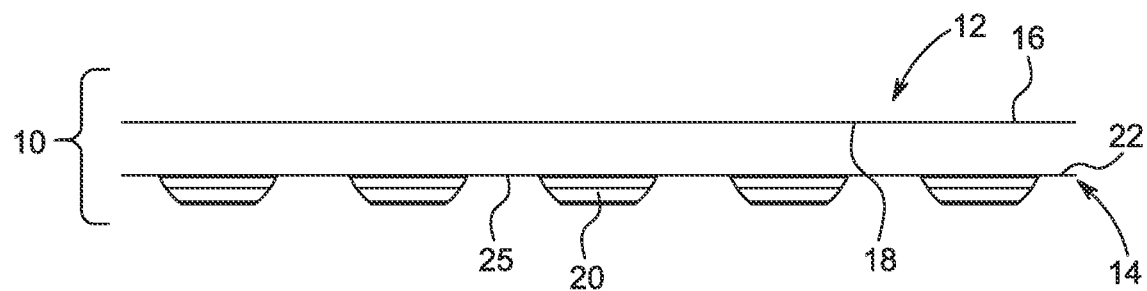
FIG. 1 is an exploded side view of a container for packaging a therapeutic product showing the lidding layer and the well layer.

In the following description, it is understood that other embodiments may be utilized and structural and operational changes may be made without departure from the scope of the present embodiments disclosed herein.

Definitions

As used herein, the terms "compound". "complex", and "product" are used interchangeably, and are intended to refer to a chemical entity, whether in the solid, liquid, or gaseous phase, and whether in a crude mixture or purified and isolated. Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present, and all such stable isomers are contemplated in the present disclosure. Cis- and trans- (or E- and Z-) geometric isomers, when present, may be isolated as a mixture of isomers or as separated isomeric forms. Compounds referenced in the disclosure can be isolated in optically active or racemic forms. Optically active forms may be prepared by resolution of racemic forms or by synthesis from optically active starting materials. All processes used to prepare these compounds and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions, the end products referenced in the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds may be separated into the individual isomers. Compounds referenced in the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein, the term "solvate" refers to a physical association of a referenced compound with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvent molecules which may form the solvate include, but are not limited to, water, methanol, ethanol, n-propanol, isopropanol, n-butanol, isobutanol, tert-butanol, ethyl acetate and other lower alkanols, glycerin, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g., polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

The phrase "pharmaceutically acceptable" is employed herein to refer to those compounds, materials, compositions, and/or dosage forms which are, within the scope of sound medical judgment, suitable for use in contact with the tissues of human beings without excessive toxicity, irritation, allergic response, or other problem or complication, commensurate with a reasonable benefit/risk ratio.

As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids and phenols. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990)—which is incorporated herein by reference in its entirety.

The phrase "consists essentially of" is used to describe a high degree of purity of a compound. For instance, to say that "A consists essentially of B" means that A may comprise at least 95 wt %, at least 99.0 wt %, at least 99.5 wt %, at least 99.9 wt %, at least 99.95 wt %, at least 99.99 wt %, at least 99.995 wt %, at least 99.999 wt %, or 100 wt % of B, relative to a total weight of A. or A consists of B. The phrase "A consists essentially of B" also means that A may comprise small amounts of additives, impurities, or other ingredients that are negligible and/or do not materially distinguish the properties, characteristics, or performance from 100 wt % B. When referencing a particular pharmaceutical composition/material, the phrase "consists essentially of", additionally means that the particular composition/material may include minor amounts of impurities so long as those impurities do not affect the basic and novel property of the invention—the ability to treat pain.

As used herein, the terms "optional" or "optionally" means that the subsequently described event(s) can or cannot occur or the subsequently described component(s) may or may not be present (e.g., 0 wt. %).

As used herein, the terms "treat", "treatment", and "treating" in the context of the administration of a therapy to a subject in need thereof refers to the reduction or amelioration of severity of symptoms of the condition being treated; reduction of duration of symptoms of the condition being treated; reduction, inhibition, slowing, or arresting of the progression of symptoms associated with the condition; reduction of frequency of symptoms of the condition being treated, elimination of symptoms and/or underlying cause of the condition; prevention of the occurrence of symptoms of the condition, for example in a subject that may be predisposed to the condition but does not yet experience or exhibit symptoms of the condition; improvement or remediation or amelioration of damage following a condition, for example improving, remediating, or ameliorating inflammation; and/or causing regression of the condition.

The term "pain" should be understood to include any unpleasant sensory and emotional experience associated with actual or potential tissue damage, or described in terms of such damage. This term generally includes nociceptive pain, neuropathic pain, and psychogenic pain; including any subset of pain associated therewith such as phantom pain, breakthrough pain, incident pain, inflammatory pain, post-surgical (postoperative) pain, cancer-associated pain, peripheral pain, central pain, spastic pain, and the like; as well as both acute pain and chronic pain conditions.

The term "subject" and "patient" are used interchangeably. As used herein, they refer to any subject for whom or which therapy is desired. In most embodiments, the subject is a human.

The terms "administer", "administering", "administration", and the like, as used herein, refer to the methods that may be used to enable delivery of the active therapeutic ingredient (ATI) to the desired site of biological action. Routes or modes of administration are as set forth herein.

The term "Rapid Infusion Technology™ (RITe) platform" or "rapidly infusing composition," as used herein means a solid dosage form containing medicinal substances that disintegrates rapidly in the oral cavity (when contacted with saliva) with no need for chewing or swallowing liquids (e.g., water, liquid carriers, saliva, etc.) to ingest these medicinal substances, with an in-vitro disintegration time of 30 second or less according to the United States Phamacopeia (USP) <701> Disintegration Test. The disclosed rapidly infusing compositions are thus a different dosage form than, for example, a chewable tablet or a tablet that should be swallowed whole with food or liquid.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount" or "therapeutically effective amount" refer to a sufficient amount of an active therapeutic ingredient (ATI) being administered which provides the desired therapeutic or physiological effect or outcome, for example, the amount of ATI sufficient for relieving to some extent one or more of the pain symptoms of the condition being treated. The result can be a reduction and/or alleviation of the signs, symptoms, or causes of a disease, or any other desired alteration of a biological system. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the age and general condition of the subject, mode of administration, and the like. An appropriate "effective amount" in any individual case may be determined by one of ordinary skill in the art using only routine experimentation, for example through the use of dose escalation studies.

Lidding Layer and Well Layer Structure

The present disclosure is directed to a container 10 for packaging a therapeutic product, which is made of a substantially planar lidding layer 12 and a well layer 14, each comprising a multilayer structure. The lidding layer 12 has an interior lid side 18 removably attached to an interior well side 22 of the well layer. The well layer is shaped to form one or more pockets 20 between the interior lid side 18 and the interior well side 22, where each pocket is configured to enclose a therapeutic product 54.

Figure 4:
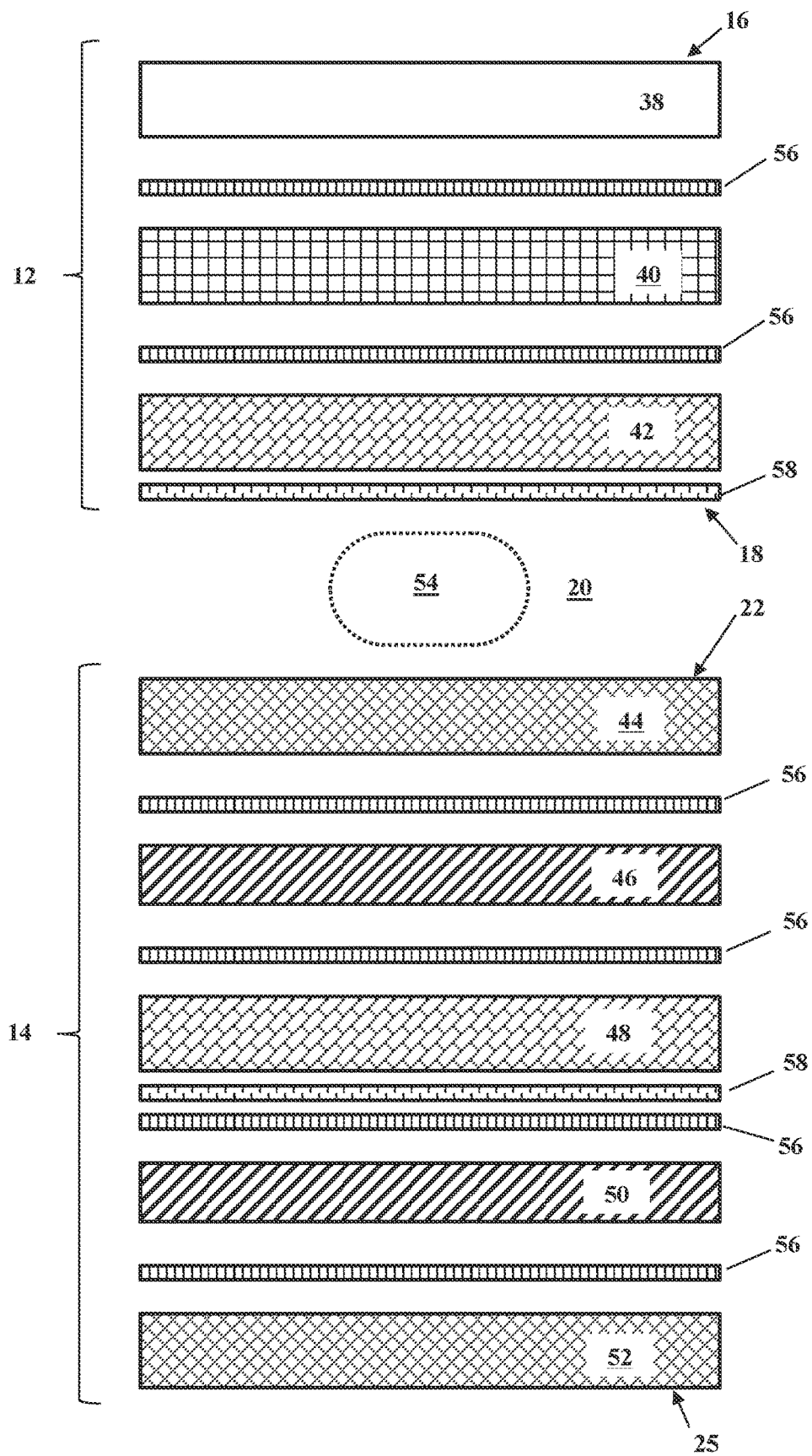
FIG. 4 shows the structure and orientation of the lidding layer and the well layer.

In one embodiment, as shown in FIG. 4, the lidding layer 12 comprises, in order from an exterior lid side 16 to the interior lid side 18; a labeling layer 38; a thermoplastic polymer lidding layer 40; and an aluminum lidding layer 42.

In one embodiment, the lidding layer 12 has an average layer thickness of at least 90 µm, at least 92 µm, at least 94 µm, at least 96 µm, at least 98 µm, at least 100 µm, at least 102 µm, at least 104 µm, at least 106 µm, at least 108 µm, at least 110 µm, and/or up to 130 µm, up to 128 µm, up to 126 µm, up to 124 µm, up to 122 µm, up to 120 µm, up to 118 µm, up to 116 µm, up to 114 µm, up to 112 µm, up to 110 µm, up to 108 µm.

In one embodiment, the lidding layer 12 has a mass per area of at least 100 g/m$^2$, at least 110 g/m$^2$, at least 120 g/m$^2$, at least 130 g/m$^2$, at least 140 g/m$^2$, at least 145 g/m$^2$, and/or up to 200 g/m$^2$, up to 190 g/m$^2$, up to 180 g/m$^2$, up to 170 g/m$^2$, up to 160 g/m$^2$, up to 155 g/m$^2$, up to 150 g/m$^2$.

In one embodiment, the well layer 14 comprises, in order from the interior well side 22 to an exterior well side 25; a first thermoplastic polymer well layer 44; a first polyamide layer 46; an aluminum well layer 48; a second polyamide layer 50; and a second thermoplastic polymer well layer 52. The five-layer cold form aluminum blister of this embodiment provides a number of benefits for manufacturing and storing a therapeutic product such as a lyophilized rapidly infusing composition, including, but not limited to: increasing rigidity of the well layer to prevent deformation during the freezing and/or lyophilization steps as well as reduce potential damage to the rapidly infusing composition itself during removal from the packaging; and enabling the formation of a quality hermetic seal to protect the tablet within.

In one embodiment, the well layer 14 has an average layer thickness of at least 190 µm, at least 195 µm, at least 200 µm, at least 205 µm, at least 210 µm, at least 215 µm, at least 220 µm, at least 225 µm, at least 230 µm, at least 235 µm, at least 240 µm, and/or up to 300 µm, up to 295 µm, up to 290 µm, up to 285 µm, up to 280 µm, up to 275 µm, up to 270 µm, up to 265 µm, up to 260 µm, up to 255 µm, up to 250 µm, up to 245 µm, up to 240 µm, up to 235 µm, up to 230 µm.

In one embodiment, the well layer 14 has a mass per area of at least 320 g/m$^2$, at least 330 g/m$^2$, at least 340 g/m$^2$, at least 350 g/m$^2$, at least 360 g/m$^2$, at least 370 g/m$^2$, at least 380 g/m$^2$, at least 390 g/m$^2$, and/or up to 460 g/m$^2$, up to 450 g/m$^2$, up to 440 g/m$^2$, up to 430 g/m$^2$, up to 420 g/m$^2$, up to 400 g/m$^2$, up to 395 g/m$^2$.

In one embodiment, the thermoplastic polymer lidding layer 40, the first thermoplastic polymer well layer 44, and/or the second thermoplastic polymer well layer 52; the aluminum lidding layer and/or the aluminum well layer 42/48; and the first and/or second polyamide layer 46/50 each independently has an average layer thickness of at least at least 5 µm, at least 8 µm, at least 10 µm, at least 12 µm, at least 15 µm, at least 18 µm, at least 20 µm, at least 22 µm, at least 25 µm, at least 28 µm, at least 30 µm, at least 32 µm, at least 35 µm, at least 38 µm, at least 40 µm, at least 42 µm, at least 45 µm, at least 48 µm, at least 50 µm, at least 52 µm, at least 55 µm, at least 58 µm, at least 60 µm, at least 62 µm, at least 65 µm, at least 68 µm, at least 70 µm, at least 72 µm, at least 75 µm, at least 78 µm, at least 80 µm, and/or up to 120 µm up to 115 µm, up to 110 µm, up to 105 µm, up to 100 µm, up to 95 µm, up to 90 µm, up to 85 µm, up to 82 µm, up to 80 µm, up to 78 µm, up to 75 µm, up to 72 µm, up to 70 µm, up to 68 µm, up to 65 µm, up to 62 µm, up to 60 µm, up to 58 µm, up to 55 µm, up to 52 µm up to 50 µm, up to 48 µm, up to 45 µm, up to 42 µm, up to 40 µm up to 38 µm, up to 35 µm, up to 32 µm, up to 30 µm, up to 28 µm, up to 25 µm, up to 22 µm, up to 20 µm, up to 18 µm, up to 15 µm, up to 12 µm, up to 10 µm. In a preferred embodiment, the thermoplastic polymer lidding layer 40 has a thickness of approximately 23 µm, the aluminum lidding layer 42 has a thickness of approximately 20 µm, the first thermoplastic polymer well layer 44 and the second thermoplastic polymer well layer 52 each has a thickness of approximately 60 µm, the aluminum well layer 48 has a thickness of approximately 60 µm, and the first polyamide layer 46 and the second polyamide layer 50 each has a thickness of approximately 25 µm.

In one embodiment, the lidding layer 12 and the well layer 14 are opaque and total barriers to light and UV radiation. In another embodiment, the layers each have low moisture vapor transmission rates (MVTR) and low oxygen transmission rates (OTR).

Moisture vapor transmission rate (MVTR), also called water vapor transmission rate (WVTR), is a measure of the passage of water vapor through a substance. It is a measure of the permeability for vapor barriers, where a lower MVTR indicates better performance as a barrier. The MVTR is measured as the mass of water that permeates through an area of a planar substance per day, at a warm temperature and high humidity. In one embodiment, the lidding layer 12 and the well layer 14 each independently have a MVTR of less than 0.1 g/m$^2$/day measured at 38° C. and 90% relative humidity, preferably less than 0.05 g/m$^2$/day, preferably less than 0.01 g/m$^2$/day. A typical MVTR for a 250 µm thick blister pack laminate layer comprising PVC is around 0.1 g/m$^2$/day under the same temperature and humidity conditions. In a preferred embodiment, a lidding layer 12 constructed as described above having a thickness of approximately 108 µm and a well layer 14 constructed as described above having a thickness of approximately 245 µm each independently have a MVTR of less than 0.01 g/m$^2$/day under the same temperature and humidity conditions, which is effectively a moisture vapor transmission rate that is below detectable levels.

Similarly, the oxygen transmission rate (OTR) is a measure of the volume of oxygen that passes through an area of a planar substance per day at a moderate temperature and humidity. In one embodiment, the lidding layer 12 and the well layer 14 each independently have an OTR of less than 0.1 mL/m$^2$/day measured at 23° C. and 500% relative humidity, preferably less than 0.05 mL/m$^2$/day, preferably less than 0.01 mL/m$^2$/day, preferably less than 0.005 mL/m$^2$/day. A typical OTR for a 250 µm thick blister pack laminate layer comprising PVC is around 20 mL/m$^2$/day under the same temperature and humidity conditions. In a preferred embodiment, a lidding layer 12 constructed as described above having a thickness of approximately 108 µm and a well layer 14 constructed as described above having a thickness of approximately 245 µm each independently have a OTR of less than 0.005 mL/m$^2$/day under the same temperature and humidity conditions, which is effectively an oxygen transmission rate that is below detectable levels.

Layer Compositions

In one embodiment, the labeling layer 38 comprises paper or some other surface suitable for printing, labeling, or marking. The paper may be one or similar to one selected from the group consisting of parchment paper, blotting paper, lens paper, bond paper, cardstock, cartridge paper, construction paper, cotton paper, kraft paper, laid paper, manila paper, newsprint, butcher paper, wrapping paper, copy paper, thermal paper, tissue paper, tracing paper, calendared paper, and wove paper. In one embodiment, the labeling layer may further comprise a film of a polymer, such as any of those listed herein, or may be impregnated with a polymer or a pigment. In one embodiment, the labeling layer may be marked by engraving, embossing, or etching, for instance, by laser etching. In an alternative embodiment, a lidding layer does not comprise a labeling layer; instead, the thermoplastic polymer lidding layer is able to provide a function of being labeled or marked. In one embodiment, the labeling layer may be marked or printed and then covered with a transparent polymer film.

In one embodiment, the labeling layer may be considered a sticker. In one embodiment, the labeling layer may not be a continuous sheet and may have an area smaller than the first thermoplastic layer 40 or the aluminum lidding layer 42. In one embodiment, a labeling layer may only be present in a region of the labeling layer above each pocket. In one embodiment, a label on the labeling layer may be reproduced above each pocket. In another embodiment, a label may indicate where to open the container, or may indicate the identity of the therapeutic product.

In one embodiment, the thermoplastic polymer lidding layer 40, the first thermoplastic polymer well layer 44, and the second thermoplastic polymer well layer 52 each independently comprise a thermoplastic polymer. As described here, a "thermoplastic" material is a linear or branched polymer which can be repeatedly softened and made flowable when heated and then returned to a hard state when cooled to room temperature. It generally has an elastic modulus greater than 10,000 psi in accordance with the method of ASTM D638. In addition, thermoplastics can be molded or extruded into articles of any predetermined shape when heated to the softened state. In the context of the present invention the thermoplastic polymers are formed as films.

In one embodiment, the thermoplastic polymer is selected from, but not limited to, a fluoropolymer, a polyarylether ketone, a polyether, a polyester, a polyamide, an oriented polyamide, a polyimide, a polyurethane, a polycarbonate, a polyanhydride, a polyurea, a polyolefin, a polystyrene, a polysulfone, a polysulfide, a polyketone, a poly(methyl acrylate), a polymethacrylamide, a vinyl polymer, a polysiloxane, a polyvinylfluoride (PVF), a polyvinylidene fluoride (PVDF), a polytetrafluoroethylene (PTFE), a polychlorotrifluoroethylene (PCTFE), a perfluoroalkoxy (PFA) polymer, a fluorinated ethylene-propylene (FEP) copolymer, a polyethylenetetrafluoroethylene, a polyethylene chlorotrifluoroethylene (ECTFE), a poly(chlorotrifluoroethylene-co-vinylidene fluoride), a perfluoropolyether (PFPE), a perfluorosulfonic acid, an acrylonitrile butadiene styrene (ABS) copolymer, a styrene-butadiene copolymer, a styrene-acrylonitrile copolymer, an ethylene-vinyl acetate (EVA) copolymer, an ethylene vinyl alcohol copolymer (EVOH), a polyethylene terephthalate (PET), a poly cyclohexylene dimethylene terephthalate (PCT), a polyhydroxyalkanoate, a polyethylene (PE), a polyetheretherketone (PEEK), a polyetherketoneketone (PEKK), a polyetherimide (PET), a polyethersulfone (PES), a polylactic acid (PLA), a polyglycolic (PGA), a poly(lactic-co-glycolic acid) (PLGA), a polymethylpentene (PMP), a polyphenylene oxide (PPO), a polyphenylene sulfide (PPS), a polypropylene (PP), an oriented polypropylene, a polystyrene (PS), a polytrimethylene terephthalate (PTT), a polyvinyl acetate (PVA), a polyvinyl chloride (PVC), a polyvinylidene chloride (PVDC), a polyvinylidenechloride methylacrylate copolymer (PVDC-MA), a polydicyclopentadiene (PDCPD), a polyacrylonitrile (PAN), a cyclic olefin copolymer (COC), cellulose acetate phthalate (CAP), hydroxypropyl methylcellulose phthalate (HPMCP), polyvinyl acetate phthalate (PVAP), hydroxypropylmethyl cellulose, hydroxypropyl methylcellulose acetate succinate (HPMCAS), cellulose acetate trimellitate, hydroxypropyl methylcellulose succinate, carboxymethyl cellulose, carboxymethyl ethyl cellulose, cellulose acetate phthalate, cellulose acetate succinate, cellulose acetate hexahydrophthalate, cellulose propionate phthalate, cellulose acetate maleate, cellulose acetate butyrate, cellulose acetate propionate, a copolymer of methylmethacrylic acid and methyl methacrylate, a copolymer of methyl acrylate, methylmethacrylate and methacrylic acid, a copolymer of methylvinyl ether and maleic anhydride, polyvinyl acetate phthalate, zein, shellac, Eduragit L 30 D-55, Eudragit FS 30 D, Eudragit L 100, Eudragit S 100, Kollicoat EMM 30D, Estacryl 30D, or any mixture thereof.

In one embodiment the thermoplastic polymer has a weight average molecular weight, or a number average molecular weight, of at least 1 kDa, at least 10 kDa, at least 50 kDa, at least 100 kDa, at least 200 kDa, at least 400 kDa, at least 500 kDa, at least 600 kDa, at least 800 kDa, and/or up to 900 kDa, up to 800 kDa, up to 700 kDa, up to 600 kDa, up to 500 kDa, up to 400 kDa, up to 300 kDa, up to 200 kDa, up to 100 kDa, up to 50 kDa.

In one embodiment, the thermoplastic polymer lidding layer 40, the first thermoplastic polymer well layer 44, and the second thermoplastic polymer well layer 52 each independently comprise at least one polymer selected from the group consisting of polyvinylchloride, polyethylene terephthalate, polyamide, polyethylene, poly(lactic-co-glycolic acid), polytetrafluoroethylene, polyvinylidene fluoride, polylactic acid, polypropylene, polystyrene, polyvinyl acetate, and polyvinylidene chloride.

In one embodiment, the first and second thermoplastic polymer well layers 44/52 comprise or consist essentially of polyvinylchloride. In one embodiment, a residual vinyl chloride monomer content in the first and/or second thermoplastic polymer well layers is less than 10 ppb, less than 5 ppb, less than 1 ppb.

In one embodiment, the thermoplastic polymer lidding layer 40 comprises or consists essentially of polyethylene terephthalate (PET).

In an alternative embodiment, the aluminum lidding layer and/or the aluminum well layer may be replaced by layers of other metals, for instance, each independently comprising at least one metal selected from the group consisting of Fe, Ti, Mo, Cu, Ni, Sn, Mn, Mg, Cr, Co, In, Sn, Zn, V, and Ti. In one embodiment a stainless steel layer may be used. In one embodiment, the aluminum lidding layer and/or the aluminum well layer may comprise an aluminum alloy. The aluminum alloy may be a 1000 series alloy, a 2000 series alloy, a 3000 series alloy, a 4000 series alloy, a 5000 series alloy, a 6000 series alloy, a 7000 series alloy, an 8000 series alloy, an alferium alloy, an alclad alloy, a Birmabright® alloy, a Duralumin® alloy, a Hindalium® alloy, a Pandalloy® alloy, a magnalium alloy, a magnox alloy, a silumin alloy, a Titanal® alloy, an alnico alloy, or some other alloy. In one embodiment, the aluminum lidding layer and the aluminum well layer consist essentially of aluminum. In one embodiment, the aluminum lidding layer and the aluminum well layer 42/48 are used to block ambient light and UV radiation from penetrating into the pockets 20.

In one embodiment, the first and second polyamide layers 46/50 each independently comprise an aromatic aldehyde. The aromatic aldehyde may be at least one selected from the group consisting of ortho-phthaladehyde, benzaldehyde, 2-methoxybenzaldehyde, 2-methylbenzaldehyde, 3-acetyl-6-methoxybenzaldehyde, 2-aminobenzaldehyde, 4-anisaldehyde, 3-bromobenzaldehyde, 2-carboxybenzaldehyde, 4-carboxybenzaldehyde, 2-chlorobenzaldehyde, cuminaldehyde, dimethoxybenzaldehyde, 2,4-dimethoxybenzaldehyde, 2,5-dimethoxybenzaldehyde, para-dimethylaminobenzaldehyde, 4-ethylbenzaldehyde, 4-formylphenylboronic acid, helicin, hericenone, hemandaline, 4-methylbenzaldehyde, nitrobenzaldehyde, 2-nitrobenzaldehyde, 3-nitrobenzaldehyde, 4-nitrobenzaldehyde, phthalaldehyde, piperonal, 3,4,5-trimethoxybenzaldehyde, and veratraldehyde.

In one embodiment, the first and second polyamide layers 46/50 comprise a polyamide. The polyamide may be an oriented polyamide, an aliphatic polyamide, a semi-aromatic amide or polyphthalamide, an aromatic polyamide, or a nylon.

In one embodiment, the first and second polyamide layers 46/50 comprise oriented polyamide (oPA). In one embodiment, the first and/or second polyamide layers consist essentially of oriented polyamide.

In one embodiment, two or more adjacent layers of the lidding layer 12 and/or of the well layer 14 are held together by an adhesive 56 or a lacquer interlayer 58. In one embodiment the lidding layer 12 and the well layer 14 are attached to each other by an adhesive. In a related embodiment, the exterior side of the lidding layer 16, the interior side of the lidding layer 18, the interior side of the well layer 22, and/or the exterior side of the well layer 25 may comprise one or more lacquer layers. In one embodiment, the interior side of the lidding layer 18 comprises two lacquer layers. The adhesive and lacquer layer may have an average layer thickness of at least 0.5 μm, at least 1 μm, at least 2 μm, at least 3 μm, at least 4 μm, at least 5 μm, at least 6 μm, at least 7 μm, at least 8 μm, at least 9 μm, at least 10 μm and/or up to 15 μm, up to 14 μm, up to 13 μm, up to 12 μm, up to 11 μm, up to 10 μm, up to 9 μm, up to 8 μm, up to 7 μm, up to 6 μm, up to 5 μm up to 4 μm, up to 3 μm, up to 2 μm, up to 1 μm.

In one embodiment, the adhesive 56 may be a thermoplastic (hot-melt) rubber resin adhesive, a solvent-based resin adhesive, a polyphenol resin, an epoxy, a silicone-based adhesive, a polyvinyl acetate based adhesive, a polyurethane-based adhesive, a thermoplastic or thermosetting plastic, or an acrylic polymer based adhesive. In one embodiment, the adhesive may be a two-part polyurethane-based adhesive. In one embodiment, the adhesive may comprise an acrylic polymer based adhesive or resin, such as polymers formed from methacrylate, cyanoacrylate, methyl methacrylate, ethyl acrylate, 2-chloroethyl vinyl ether, 2-ethylhexyl acrylate, hydroxyethyl methacrylate, butyl acrylate, butyl methacrylate, or trimethylolpropane triacrylate (TMPTA) monomers, or mixtures thereof. In one embodiment, the adhesive comprises a cyanoacrylate monomer, in reacted form. The cyanoacrylate may be methyl cyanoacrylate, ethyl cyanoacrylate, butyl cyanoacrylate, octyl cyanoacrylate, and/or 2-octyl cyanoacrylate. The adhesive may be doped with other compounds such as phthalic anhydride, poly(methyl methacrylate), hydroquinone, or sulfonic acid in order to adjust physical and chemical properties such as viscosity, curing speed, or adhesion strength. These other compounds may be doped at a weight percent of 0.01-10 wt %, preferably 0.1-5.0 wt %, more preferably 0.2-3.0 wt % relative to a total weight percentage of the adhesive.

In one embodiment, the lacquer 58 is a cross-linked polymer resin. As used herein, "cross-linking" or a "cross-link" refers to polymers and resins containing branches that connect polymer chains via bonds that link one polymer chain to another. The cross-link may be an atom, a group of atoms, or a number of branch points connected by bonds, groups of atoms, or polymer chains. In the majority of cases, a cross-link is a covalent structure or covalent bond, but the term may also describe sites of weaker chemical interactions, portions of crystallites, and even physical interactions and entanglements. The cross-linking can alter the physical and mechanical properties of the polymer. Cross-linking may be formed by chemical reactions that are initiated by heat, pressure, change in pH, and/or radiation, with or without the presence of a cross-linking agent and/or catalyst. As used herein, a "resin" refers to a solid or highly viscous substance or polymeric macromolecule containing polymers, preferably with reactive groups. The cross-linked polymer resin may be an epoxy polymer resin, a phenolic resin, an acrylic resin, a vinyl acetate resin, or may be an adhesive as listed previously. In one embodiment, the lacquer is applied in a liquid state. In one embodiment, the lacquer is used for heat sealing, and may be considered a heat seal coating.

In alternative embodiments, the lidding layer 12 and/or the well layer 14 may comprise one or more thermoplastic polymer layers, aluminum layers, polyamide layers, and labeling layers in different orders, or may comprise fewer layers than previously described or may comprise more layers than previously described. In one embodiment, a thermoplastic polymer layer, an aluminum layer, a polyamide layer, and/or a labeling layer may further comprise an additive such as a stabilizer, filler, a mineral particle, calcium carbonate, aluminum silicate, a fatty acid, a carbon black, a plasticizer, an absorbent, an adsorbent, a binder, a lubricant, a pigment, and/or a colorant. In another embodiment, the thermoplastic polymer layer, aluminum layer, polyamide layer, and/or a labeling layer may not comprise an additive. In one embodiment, the lidding layer 12 and/or the well layer 14 may further comprise a silicone layer or an absorbent/adsorbent layer.

Container Structure

In one embodiment, the container has a length of at least 4 cm, at least 6 cm, at least 8 cm, at least 10 cm, at least 12 cm, and/or up to 25 cm, up to 24 cm, up to 22 cm, up to 20 cm, up to 18 cm, up to 16 cm, up to 14 cm.

In one embodiment, the container has a width of at least 2 cm, at least 3 cm, at least 4 cm, at least 5 cm, and/or up to 15 cm, up to 13 cm, up to 12 cm, up to 10 cm, up to 8 cm, up to 7 cm.

As mentioned previously, the lidding layer 12 has an interior lid side 18 removably attached to an interior well side 22 of the well layer 14. The well layer is substantially planar where it attaches to the lidding layer. The well layer is shaped to form one or more pockets 20 between the interior lid side and the interior well side, where each pocket is configured to enclose a therapeutic product 54.

In one embodiment, each pocket 20 has a volume in a range of at least 0.3 cm$^3$, at least 0.4 cm$^3$, at least 0.5 cm$^3$, at least 0.6 cm$^3$, and/or up to 4 cm$^3$, up to 3.5 cm$^3$, up to 3.0 cm$^3$, up to 2.5 cm$^3$, up to 2.0 cm$^3$, up to 1.8 cm$^3$, up to 1.5 cm$^3$, up to 1.2 cm$^3$, up to 1.0 cm$^3$.

In one embodiment, each pocket 20 has a vertical depth in a range of at least 3 mm, at least 3.2 mm, at least 3.5 mm, at least 3.8 mm, at least 4 mm, at least 4.5 mm, at least 5 mm, and/or up to 10 mm, up to 9.5 mm, up to 9.0 mm, up to 8.5 mm, up to 8.0 mm, up to 7.5 mm, up to 7.0 mm, up to 6.5 mm, up to 6.0 mm, up to 5.5 mm, up to 5.0 mm.

Figure 2:
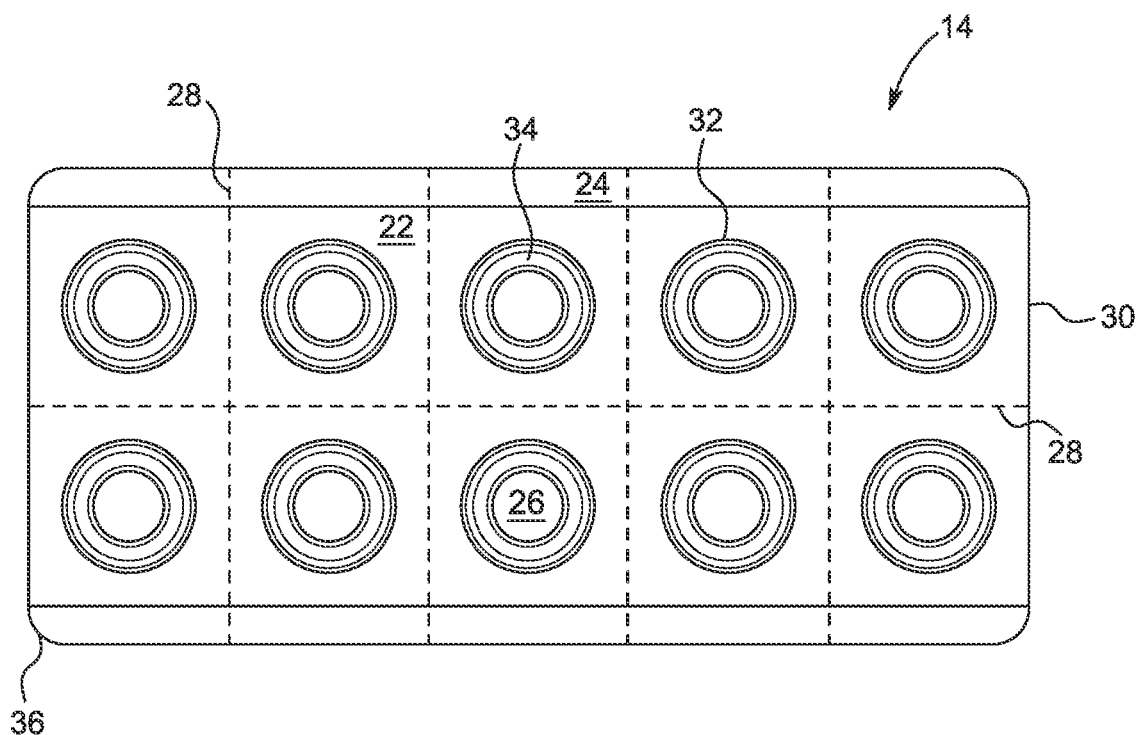
FIG. 2 is a top view of the well layer.
Figure 3:
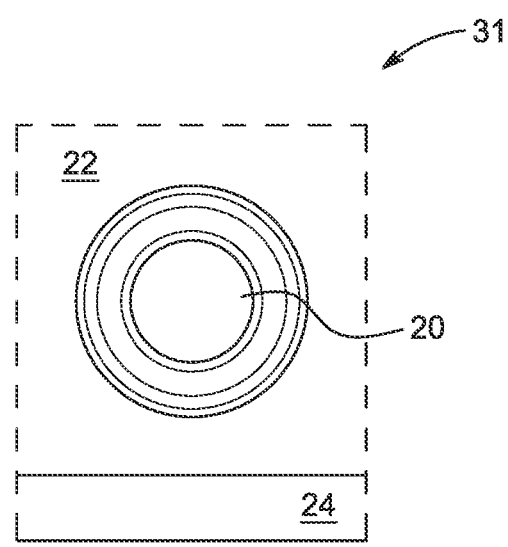
FIG. 3 shows the well layer of an individual blister unit.

In one embodiment, the one or more pockets 20 are each rotationally symmetric about a central axis and have a substantially flat portion 26 and non-convex sidewalls. FIGS. 1-3 show pockets 20 with such shapes. In this context, "substantially flat" should be understood to include a surface that has a raised or lowered portion(s) in order to deboss or emboss a logo or other information into the therapeutic product.

Figure 6:
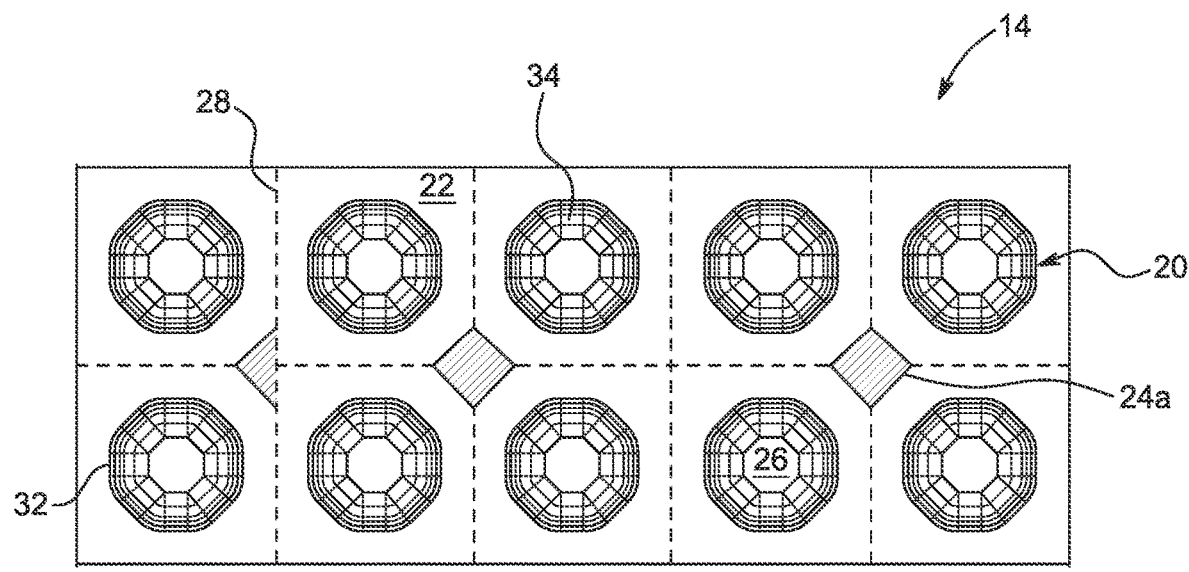
FIG. 6 shows a top view of a well layer having facetted interior sidewalls.
Figure 7:
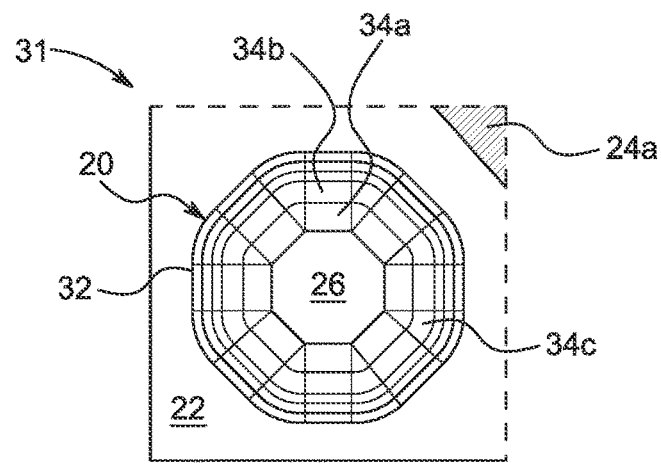
FIG. 7 shows the well layer of an individual blister unit having facetted interior sidewalls.

In one embodiment, the one or more pockets 20 are rotationally symmetric about a central axis with 3, 4, 5, 6, 7, 8, 9, 10, or 12-fold symmetry, preferably 8-fold symmetry as shown by the pockets 20 in FIGS. 6 and 7.

In one embodiment, the pockets may be considered frustoconical. In one embodiment, the interior sidewalls 34 are formed at a fixed angle, for instance, the interior angle formed between the sidewall 34 and the substantially flat portion 26 of the pocket may be at least 90°, at least 100°, at least 110°, at least 120° at least 130°, at least 135°, at least 140° at least 145° and/or up to 150°, up to 145°, up to 135°, up to 130°, up to 125°, up to 120°, up to 110°, up to 100°.

In one embodiment, the sidewall interior angle is about 90° so that the sidewalls 34 are substantially cylindrical. In other embodiments, the pockets 20 may be prismatic, ellipsoidal, spherical, or other concave shapes. In one embodiment, the pockets 20 may have facetted shapes, for instance, with one or more portions of the sidewalls 34 having planar faces. In another embodiment, the sidewalls may have a plurality of planar faces, similar to a cut gemstone.

Figure 5:
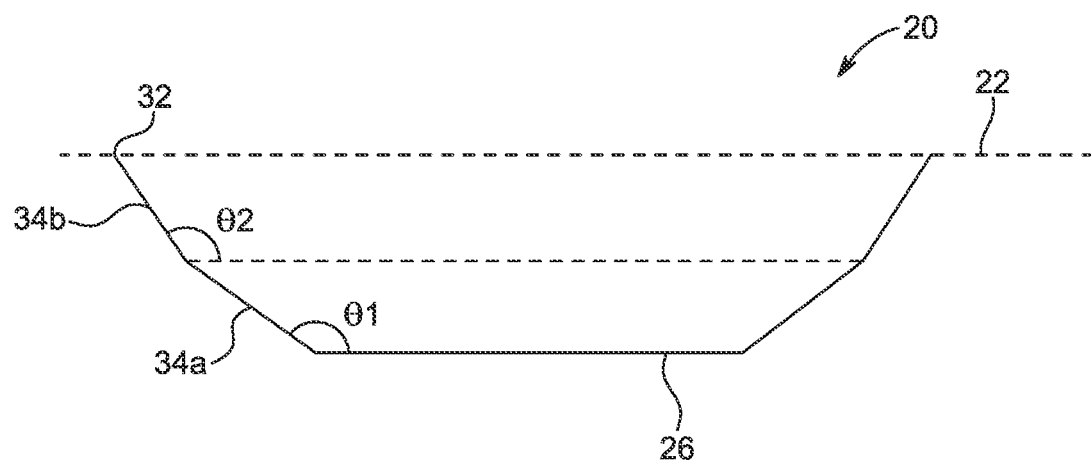
FIG. 5 shows a cross-sectional view of an individual pocket.

In one embodiment, the sidewalls 34 can be separated into two or more sections, e.g. a lower section 34a and an upper section 34b as shown in FIGS. 5 and 7.

In one embodiment, each section 34a/34b has a vertical height as measured perpendicular to the interior side of the well layer 22. The vertical height of the upper section 34b may be at least 10%, at least 20%, at least 30%, at least 40%, at least 50%, at least 60%, at least 70%, at least 80% and/or at most 90%, at most 80%, at most 70%, at most 60%, at most 50%, at most 40%, at most 30%, at most 20% of the combined vertical heights of the upper and lower sections 34a/34b.

In one such embodiment, each of the sections 34a/34b is frustoconical and the interior angle ($\theta 1$) between the substantially flat portion 26 and the lower portion of the sidewall 34a is greater than the angle ($\theta 2$) between the upper portion of the sidewall 34b and a plane parallel to the substantially flat portion 26 as shown in FIG. 5. In one such embodiment, $\theta 1$ may be greater than $\theta 2$ by at least 50, at least 10°, at least 20°, at least 30°, at least 40°, at least 50°, at least 60°, at least 70°, and/or most 10°, at most 20°, at most 30°, at most 4°, at most 50°, at most 60°, at most 70° at most 80°.

In one embodiment, either one or both sections 34a/34b are frustoconical, and $\theta 1$ and/or $\theta 2$ are each independently an angle of at least 90°, at least 95°, at least 100°, at least 110°, at least 120°, at least 130°, at least 140°, at least 150°, at least 160°, at least 170°, at least 175° and/or at most 175° at most 170°, at most 160°, at most 150°, at most 140°, at most 130°, at most 120°, at most 110°, at most 1000, at most 95°.

Alternatively, one or both sidewall sections, 34a and 34b, could be curved. In one particular embodiment where the sidewall sections are curved, each lower section, e.g. 34a, is more concave than each succeeding upper section, e.g. 34b. In one embodiment, where the lower section 34a has greater concavity than the upper section 34b, the radius of curvature of the lower section may be at least 10%, at least 20%, at least 30%, at least 40%, at least 50%, at least 60%, at least 70%, at least 80% and/or at most 90%, at most 80%, at most 70%, at most 60%, at most 50%, at most 40%, at most 30%, at most 20% of the radius of curvature of the upper section. In other embodiments, one or both sidewall sections 34a and 34b are curved with a cross-sectional geometry showing a spherical curve, an elliptical curve, a Bezier curve, or some other curve.

In one embodiment, each of the sections 34a/34b are frustoconical but are joined by a curved segment at the interior side of the well layer 22 and the upper sidewall section 34b, at the lower and upper sidewall sections 34a/34b, or at the lower sidewall section 34a and the substantially flat portion 26. In one embodiment, this curved section may have a radius of curvature of at least 0.1 mm, at least 0.2 mm, at least 0.3 mm, at least 0.4 mm, at least 0.5 mm, at least 0.6 mm, at least 0.7 mm, at least 0.8 mm, at least 0.9 mm, at least 1.0 mm, at least 1.2 mm, at least 1.5 mm, at least 1.7 mm, at least 1.9 mm and/or at most 2.0 mm, at most 1.8 mm, at most 1.6 mm, at most 1.3 mm, at most 1.1 mm, at most 1.0 mm, at most 0.9 mm, at most 0.8 mm, at most 0.7 mm, at most 0.6 mm, at most 0.5 mm, at most 0.4 mm, at most 0.3 mm, at most 0.2 mm.

In one embodiment, each of the sections 34a/34b are planar faces, and may be joined at angles as described above. For instance, FIG. 7 shows sections 34a/34b that are each rectangular. A sidewall having planar faces may comprise other shapes, for instance, circular sections, triangular sections 34c, square sections, pentagonal sections, hexagonal sections, or octagonal sections. In one embodiment, a sidewall may comprise a combination of both planar and curved sections.

These sidewall geometries as described above not only assist with the release of the tablet for the consumer prior to consumption, but work to minimize the frost heave caused by the upward swelling of the tablet surface as the unit crystalizes and increase the ice content during the controlled freezing step.

In one embodiment, wherein the one or more pockets 20 each has sloped or curved interior sidewalls 34, a top diameter of the pocket measured where it connects with the substantially planar portion of the well layer (the top rim 32) will be greater than the bottom diameter of the pocket. In one embodiment, the top diameter may be at least 8 mm, at least 9 mm, at least 10 mm, at least 11 mm, at least 12 mm, at least 13 mm, at least 14 mm, at least 15 mm, and/or up to 25 mm, up to 20 mm, up to 18 mm, up to 17 mm, up to 16 mm, up to 15 mm, up to 14 mm, up to 13 mm. In one embodiment, the bottom diameter may be at least 5 mm, at least 7 mm, at least 8 mm, at least 9 mm, at least 10 mm, at least 11 mm, at least 12 mm, and/or at most 15 mm, at most 13 mm, at most 12 mm, at most 10 mm. Where the bottom interior 26 and/or the top rim 32 of a pocket 20 is a polygon, such as an octagon as shown in FIGS. 6, 7, and 8 the top and bottom diameters may be the greatest distance through the geometric center of the polygon, the smallest distance through the geometric center of the polygon, or the median of the greatest and smallest distances.

Figure 8:
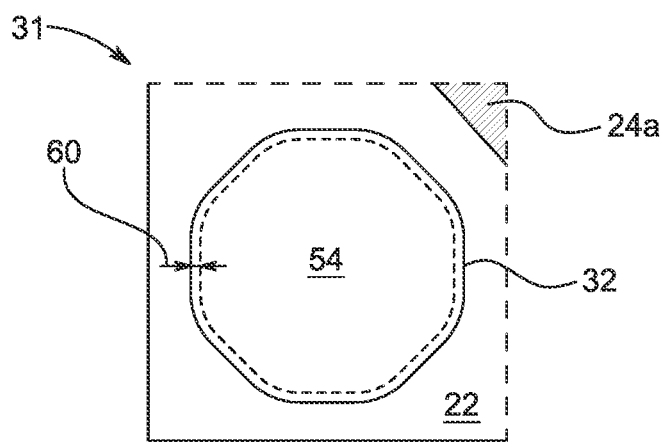
FIG. 8 shows the well layer of an individual blister unit containing an octagon-shaped product.

One of the key parameters for maintaining low moisture vapor transmission rates (MVTR) and low oxygen transmission rates (OTR) is the minimum length of the sealed region 60 between the top rim 32 of the pocket and the edge of the product 54 as shown in FIG. 8. For example, that minimum distance would be the same on both a circular-shaped pocket and an octogon-shaped pocket with each of its sides along tangents of the circular-shaped pocket. However, the octagon-shaped pocket would contain more volume, allowing for a larger dose, while maintaining similar MVTR and OTR performance.

In one embodiment, a container having a single pocket may be considered a blister unit. FIG. 3 shows a well layer of an individual blister unit 31. In other embodiments, a container may have at least two pockets, where the lidding layer and the well layer have a perforated line 28 between the at least two pockets so that the two pockets may be separated along the perforations to form individual blister units.

In one embodiment, the lidding layer 12 and the well layer 14 form at least three pockets separated by at least two perforated lines, and each adjacent two perforations are spaced by a distance in a range of at least 20 mm, at least 22 mm, at least 24 mm, and/or up to 50 mm, up to 45 mm, up to 40 mm, up to 35 mm, up to 30 mm. In one embodiment, the centers of each adjacent two pockets are spaced by the same distances: at least 20 mm, at least 22 mm, at least 24 mm, and/or up to 50 mm, up to 45 mm, up to 40 mm, up to 35 mm, up to 30 mm.

In one embodiment, the perforations are dots, pinholes, or substantially circular holes. Here, the dots, pinholes, or holes may have an inner diameter of at least 0.05 mm, at least 0.1 mm, at least 0.3 mm, at least 0.5 m, at least 1.0 mm, and/or up to 2.0 mm, up to 1.5 mm, up to 1.0 mm, up to 0.8 mm, up to 0.5 mm. In one embodiment, the perforations may be considered micro perforations. In another embodiment, the perforations may not be holes that entirely traverse both layers.

In one embodiment, the perforations may comprise elongated slits, having widths of at least 0.05 mm, at least 0.10 mm, at least 0.30 mm, and/or up to 1.00 mm, up to 0.85 mm, up to 0.80 mm. The slits may have aspect ratios (length: width) of at least 1.5:1, at least 1.7:1, at least 1.8:1, and/or up to 5:1, up to 4:1, up to 3:1. In some embodiments, the slits may not be a continual opening through the lidding layer 12 and/or the well layer 14, but may instead be sealed or shut by the elasticity of the material. In one embodiment, the slits may be longer, to the point where they may be considered sections where the individual blister units are not attached to one another.

In one embodiment, the perforations may be spaced by at least 0.5 mm, at least 0.7 mm, at least 0.8 mm and/or up to 1.5 mm, up to 1.2 mm, up to 1.0 mm.

In another embodiment, rather than perforations, the lidding layer 12 and/or well layer 14 may be weakened for directed separation along a line by other means. For instance, a rupture line may be formed by weakening the material of the lidding layer and/or well layer, by shaving, folding, rubbing with an abrasive material, irradiating, scoring, or etching.

However, in other embodiments, the container may comprise two or more adjacent pockets that do not have a perforation between them. In another embodiment, the container may comprise two or more pockets and may not comprise any perforations.

In one embodiment, the container may be considered a "blister pack," and may comprise at least 1 pocket, at least 2 pockets, at least 3 pockets, at least 4 pockets, at least 5 pockets, at least 6 pockets, at least 7 pockets, at least 8 pockets, at least 9 pockets, at least 10 pockets, at least 12 pockets, at least 14 pockets, at least 18 pockets, at least 20 pockets, at least 24 pockets, at least 36 pockets, at least 40 pockets, at least 45 pockets, and/or up to 50 pockets, up to 40 pockets, up to 35 pockets, up to 30 pockets, up to 25 pockets, up to 24 pockets, up to 20 pockets, up to 18 pockets, up to 16 pockets, up to 14 pockets, up to 12 pockets, up to 10 pockets, up to 9 pockets, up to 8 pockets, up to 7 pockets, up to 6 pockets, up to 5 pockets, up to 4 pockets, up to 3 pockets, up to 2 pockets. In one embodiment, the container comprises 10 pockets. In one embodiment, the container may have the pockets arranged in a rectangular grid, for instance, a 2×5 grid as shown in FIG. 2.

The well layer 14 may be hot formed or cold formed. In one embodiment, the well layer is cold formed.

In the case of cold forming, in general, an aluminum-based laminate film for a well layer is pressed into a mold by means of a stamp. The aluminum will be elongated and maintain the formed shape. These blisters are called cold form foil (CFF) blisters. The aluminum offers a near complete barrier against water and oxygen, allowing an extended product expiry date and promotes heat transfer during the freezing and lyophilization steps.

In one embodiment, the lidding layer 12 and the well layer 14 are sealed together to block light and air from an enclosed pharmaceutical agent in a pocket. In one embodiment, the lidding layer 12 and the well layer 14 are heat sealed together once product is placed in the well layer. In one embodiment, a product precursor is placed in the well layer, and then subjected to processes such as freezing and lyophilization, and then the lyophilized product is sealed. In one embodiment, more than one container 10 may be formed and sealed from a large sheet of a lidding layer and a large well layer, and then cut to form separate containers after the sealing.

Figure 9:
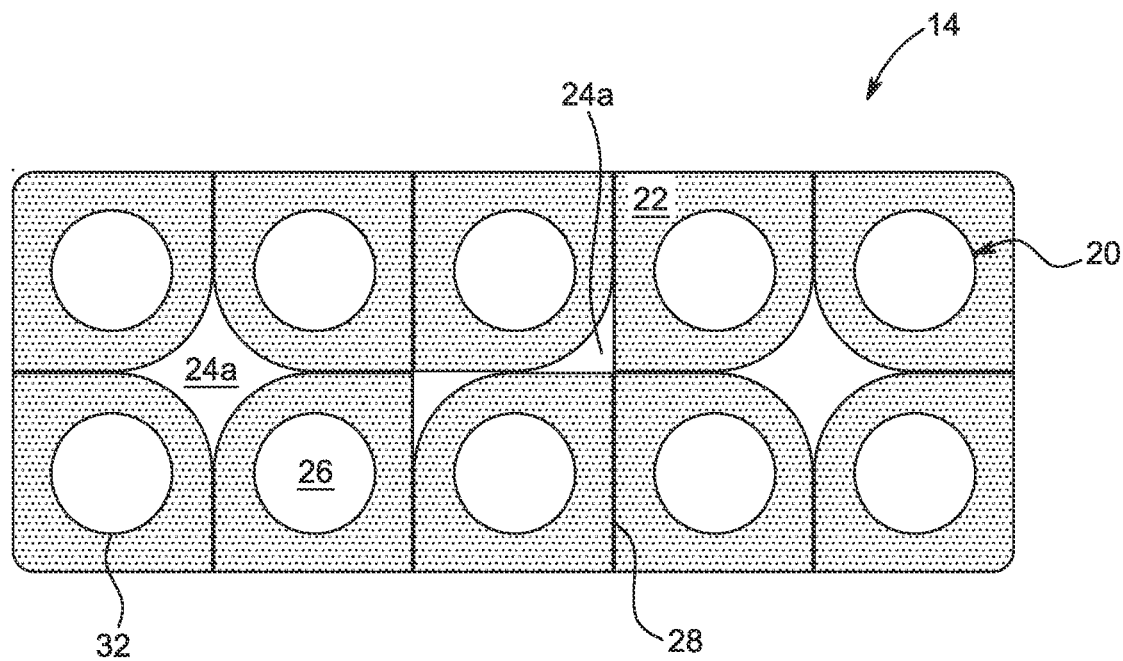
FIG. 9 shows a top view of a well layer having circular pockets and unsealed peel areas attached along a curve on the individual blister units.

In one embodiment, the therapeutic agent may be removed by peeling the lidding layer 12 from a more rigid well layer 14. In this way, the lidding layer and the well layer are removably attached to one another. Where the lidding layer is configured to be peeled off, for instance from a corner or an edge of the container 24, the lidding layer and the well layer may not be attached to each other. This edge or corner 24 may be considered an unsealed peel area. In one embodiment, the unsealed peel area may extend from the edge of the container to at least 1 mm, at least 2 mm, at least 3 mm, at least 4 mm and/or up to 10 mm, up to 8 mm, or up to 6 mm towards the pocket. FIG. 7 shows an embodiment of an unsealed peel area 24a located at a corner of an individual blister unit, FIG. 9 shows an embodiment of a well layer 14 having unsealed peel areas 24a attached along a curve of each individual blister unit. However, the container may also have edges where the lidding layer and the well layer are attached right up to the edge 30. In one embodiment, the corners of the container 10 may be rounded 36, as shown in FIG. 2.

In a related embodiment, the lidding layer 12 may extend beyond a part of the well layer 14 to provide a location for someone to start peeling, or the lidding layer may have an adhered pull tab, a fold, or some other structure to pinch and pull. In one embodiment, the lidding layer may have a textured surface in order to improve a grip when peeling the well layer.

In one embodiment, the lidding layer 12 and/or the well layer 14 are knurled where the interior lid side is removably attached to the interior well side of the well layer. The knurls may comprise ridges having a spacing of at least 0.2 mm, at least 0.4 mm, at least 0.5 mm, and/or up to 1.0 mm, up to 0.8 mm, up to 0.7 mm. In one embodiment, the knurls may result from forming the lidding layer into the well layer. In another embodiment, the knurls may serve as a texture for increasing a grip on either layer.

Drug Product Container Assembly

The present disclosure also relates to a drug product container assembly, comprising a container as described in any of the above embodiments, where at least one pocket has at least one lyophilized therapeutic product. The therapeutic product is preferably in the form of a rapidly infusing composition. Preferred rapidly infusing compositions are those suitable for administration of lipophilic active therapeutic ingredients (ATIs) such as cannabidiol (CBD) or derivative/analog thereof via a non-gastric mucosal surface. As described in more detail below, the novel RITe™ platform allows otherwise difficult to formulate ATIs—such as CBD—to be presented in unit dosage form for accurate dosing and in an easy-to-take format for high levels of patient compliance. For example, the rapidly infusing composition may be presented in tablet form and packaged in a pocket of the container, or in the pocket of an individual blister unit.

In particular, the rapidly infusing composition enables oral mucosal administration of lipophilic ATIs in a solid dosage form directly into systemic circulation via the sublingual mucosa or the buccal mucosa and avoidance of first pass metabolism. The rapidly infusing composition thus presents lipophilic ATIs such as CBD, which may be susceptible to extensive first pass metabolism, in a highly bioavailable dosage form. For example, CBD administered via the rapidly RITe™ platform herein may have a bioavailability of at least 50%, preferably at least 55%, preferably at least 60%, preferably at least 65%, preferably at least 70%, preferably at least 75%, preferably at least 80%, preferably at least 85%, preferably at least 90%, and up to 99%, preferably up to 98%, preferably up to 96%, preferably up to 95%, preferably up to 92%.

Administration may be carried out by simply placing the rapidly infusing composition directly in the buccal cavity (between the cheek and gum) or over the sublingual mucous gland (under the ventral surface of the tongue). Preferred rapidly infusing compositions are those which are lyophilized products formulated for rapid disintegration when placed in such an oral environment for rapid release of the ATI. The rapidly infusing compositions of the present disclosure may have a disintegration time of from approximately 1 second to 30 seconds or less, preferably 25 seconds or less, preferably 20 seconds or less, preferably 15 seconds or less, preferably 10 seconds or less, preferably 5 seconds or less, preferably 3 seconds or less, according to the United States Pharmacopeia (USP) <701> Disintegration Test performed in deionized water maintained at 37° C.±2°. In particular, preferred rapidly infusing compositions are those formulated for oral disintegration in 5 seconds or less, preferably 4 seconds or less, preferably 3 seconds or less, preferably 2 seconds or less, preferably in approximately 1 second, according to the United States Phamacopeia (USP) <701> Disintegration Test performed in deionized water maintained at 37° C.±2° C. A disintegration profile no higher than the above-mentioned upper limit when in intimate contact with a non-gastric mucosal surface provides for rapid absorption of the ATI and short onset times to therapeutic relief. Also, patient compliance may be improved, particularly in terms of temporary abstinence from swallowing, which is often triggered when a patient is presented with foul tasting oral medications. Any issues related to foul taste may be minimized with the above rapid disintegration times, which reduces the tendency for enteral oral administration through voluntary or involuntary swallowing, and as a result, the aforementioned high levels of bioavailability may be achieved. Given the hygroscopic and rapidly disintegrating nature of the rapidly infusing composition of the present disclosure, preferred drug product container assemblies are those having low moisture vapor transmission rates (MVTR) and low oxygen transmission rates (OTR). For instance, the drug product container assembly may comprise a container where a rapidly infusing composition is enclosed and sealed between a lidding layer and a well layer, the layers both having low MVTR and low OTR.

The rapid disintegration profile of the rapidly infusing composition, coupled with the direct introduction of the ATI into systemic circulation through the sublingual mucosa or the buccal mucosa, preferably through the buccal mucosa, provides a rapid onset of therapeutic effect. For example, the rapidly infusing composition may provide the desired pain-reduction effects in (has an onset time of) under 15 minutes, preferably under 10 minutes, preferably under 5 minutes, preferably under 4 minutes, preferably under 3 minutes, preferably under 2 minutes, preferably under 1 minute, preferably under 45 seconds, preferably under 30 seconds, preferably under 20 seconds, preferably under 10 seconds, preferably approximately 5 seconds. Such short onset times are superior to those which can be obtained with traditional orally disintegrating tablets made through compression tableting.

The rapidly infusing composition herein generally contains (a) a pharmaceutically acceptable binder and/or excipient system that includes gelatin and a sugar alcohol e.g., mannitol, and optionally one or more of a sweetener, a flavorant, and a colorant; and (b) a therapeutically effective amount of an active therapeutic ingredient such as cannabidiol (CBD) or a pharmaceutically acceptable derivative/analog, salt, or solvate thereof.

Pharmaceutically Acceptable Carrier and/or Excipient System

Carriers and/or excipients are ingredients which do not provide a therapeutic effect themselves, but which are designed to interact with, and enhance the properties of, the active therapeutic ingredient. In particular, carriers and/or excipients may act as a vehicle for transporting the active therapeutic ingredient from one organ, or portion of the body, to another organ, or portion of the body. The selection of appropriate carrier/excipient ingredients may impact the solubility, distribution, release profile/kinetics, absorption, serum stability, therapeutic onset time, and ultimately the efficacy of the ATI, as well as the shelf-life, dosage forms, and processability of the drug product. Each ingredient in the pharmaceutically acceptable carrier and/or excipient system must be "pharmaceutically acceptable" in the sense of being compatible with the other ingredients of the rapidly infusing composition and not injurious to the patient.

In light of the above, particular preference is given herein to pharmaceutically acceptable carrier and/or excipient systems which include gelatin and a sugar alcohol (e.g., mannitol).

Gelatin is to be included in the pharmaceutically acceptable carrier and/or excipient system in order to effect matrix formation in the lyophilized product, i.e., gelatin may act primarily as a matrix former. During manufacture of the rapidly infusing composition, lyophilization from an aqueous suspension results in the removal of water thereby leaving behind a gelatin matrix/scaffolding upon which the ATI can be evenly dispersed or suspended. It has been found that gelatin has a propensity to establish a stable matrix in lyophilized form, yet allow for rapid disintegration when brought into contact with the aqueous oral environment, thereby providing efficient transfer of the ATI from the hydrophilic vehicle to the oral mucosa. In this regard, bovine gelatins are preferred. In some embodiments, the rapidly infusing composition does not contain fish gelatin.

The amount of gelatin used may be varied. Generally, gelatin may be present in the rapidly infusing composition in an amount of at least 10 wt. %, preferably 12 wt. %, preferably 14 wt. %, preferably 16 wt. %, preferably 18 wt. %, preferably 20 wt. %, preferably 22 wt. %, and up to 35 wt. %, preferably up to 32 wt. %, preferably up to 30 wt. %, preferably up to 28 wt. %, preferably up to 26 wt. %, preferably up to 24 wt. %, based on a total weight of the rapidly infusing composition on a dry basis.

The pharmaceutically acceptable carrier and/or excipient system is also formulated with one or more sugar alcohols, which may act primarily as a bulking agent. Examples of sugar alcohols include, but are not limited to, erythritol, xylitol, sorbitol, maltitol, mannitol, lactitol, and glycerin, which may be used singly or in combinations. Advantage can also be taken of the effect of certain sugar alcohols in terms of taste (sweetness and coolness due to endothermal heat of solution), as well as their ability to aid/speed tablet disintegration. In this regard, particular preference is given to mannitol.

The sugar alcohol, preferably mannitol, may be present in the rapidly infusing composition in any amount which provides the desired bulking/taste/disintegration effects. Generally, this amount will range from of at least 5 wt. %, preferably at least 10 wt. %, preferably at least 12 wt. %, preferably at least 14 wt. %, preferably at least 16 wt. %, preferably at least 18 wt. %, and up to 35 wt. %, preferably up to 30 wt. %, preferably up to 28 wt. %, preferably up to 26 wt. %, preferably up to 24 wt. %, preferably up to 22 wt. %, preferably up to 20 wt. %, based on a total weight of the rapidly infusing composition on a dry basis.

In some embodiments, a weight ratio of gelatin to sugar alcohol ranges from 1:3, preferably from 1:2, preferably from 1:1, preferably from 1.1:1, and up to 3:1, preferably up to 2:1, preferably up to 1.5:1, preferably up to 1.2:1.

The pharmaceutically acceptable carrier and/or excipient system may also optionally include one or more of a sweetener, a flavorant, and a colorant.

The sweetener may be used in any amount which provides the desired sweetening effect, generally in amount of 0 to 5 wt. %, for example in an amount of up to 5 wt. %, preferably up to 4.5 wt. %, preferably up to 4 wt. %, preferably up to 3.5 wt. %, preferably up to 3 wt. %, preferably up to 2.5 wt. %, preferably up to 2 wt. %, preferably up to 1.5 wt. %, preferably up to 1 wt. %, based on a total weight of the rapidly infusing composition on a dry basis. Suitable examples of sweeteners include, but are not limited to, aspartame, saccharin (as sodium, potassium or calcium saccharin), cyclamate (as a sodium, potassium or calcium salt), sucralose, acesulfame-K, thaumatin, neohisperidin, dihydrochalcone, ammoniated glycyrrhizin, dextrose, maltodextrin, fructose, levulose, sucrose, and glucose, which may be used singly or in combinations, with particular preference given to sucralose and acesulfame-K.

It is to be readily appreciated by those of ordinary skill in the art that one or more flavorants may be optionally included in the rapidly infusing composition to mask any unpleasant taste imparted by certain ingredients (e.g., an unpleasant tasting ATI) or to otherwise impart an acceptable taste profile to the rapidly infusing composition, and the rapidly infusing composition is not limited to any particular flavor. Suitable flavorants include, but are not limited to, oil of wintergreen, oil of peppermint, oil of spearmint, oil of sassafras, oil of clove, cinnamon, anethole, menthol, thymol, eugenol, eucalyptol, lemon, lime, lemon-lime, orange, and other such flavor compounds to add fruit notes (e.g., citrus, cherry etc.), spice notes, etc., to the composition. The flavorants may be constitutionally composed of aldehydes, ketones, esters, acids, alcohols (including both aliphatic and aromatic alcohols), as well as mixtures thereof. Specific mention is made to lemon-lime flavor powder, which works particularly well with CBD as the ATI. The flavorant may be used in any amount which provides the desired flavor, generally in an amount of 0 to 5 wt. %, for example in an amount of up to 5 wt. %, preferably up to 4 wt. %, preferably up to 3 wt. %, preferably up to 2 wt. %, preferably up to 1.5 wt. %, preferably up to 1 wt. %, preferably up to 0.5 wt. %, preferably up to 0.1 wt. %, based on a total weight of the rapidly infusing composition on a dry basis.

Likewise, the rapidly infusing composition may be colored or tinted through the optional use of one or more colorants. Suitable colorants are those approved by appropriate regulatory bodies such as the FDA and those listed in the European Food and Pharmaceutical Directives and include both pigments and dyes such as FD&C and D&C dyes, with specific mention being made to FD&C Yellow #5.

In addition to gelatin and a sugar alcohol (e.g., mannitol), and optionally one or more of a sweetener, a flavorant, and a colorant, the pharmaceutically acceptable carrier and/or excipient system may optionally include one or more other pharmaceutically acceptable carriers and/or excipients known to those of ordinary skill in art, in art appropriate levels. Examples of which include, but are not limited to, fillers or extenders such as starches (e.g., corn starch and potato starch), sugars (e.g., lactose or milk sugar), high molecular weight polyethylene glycols, silicic acid, aluminum monostearate, polyesters, polycarbonates, and polyanhydrides;

binders, such as cellulose, and its derivatives, (e.g., sodium carboxymethyl cellulose, hydroxypropyl cellulose, hydroxypropylmethyl cellulose, methyl cellulose, ethyl cellulose and cellulose acetate), alginates, polyvinyl pyrrolidone, powdered tragacanth, malt, and acacia;

disintegrating agents, such as agar-agar, calcium carbonate, tapioca starch, alginic acid, certain silicates, sodium carbonate, sodium starch glycolate, and cross-linked sodium carboxymethyl cellulose;

surfactants/absorption accelerators/wetting agents/emulsifying agents/solubilizers, including any of the anionic, cationic, nonionic, zwitterionic, amphoteric and betaine variety, such as polyalkylene oxide copolymers (e.g., poloxamer), sodium lauryl sulfate, sodium dodecyl benzene sulfonate, sodium docusate, sodium lauryl sulfoacetate, alkali metal or ammonium salts of lauroyl sarcosinate, myristoyl sarcosinate, palmitoyl sarcosinate, stearoyl sarcosinate and oleoyl sarcosinate, cetyl alcohol, glycerol monostearate, polyoxyethylene sorbitol, fatty acid esters of sorbitan, polysorbates (polyalkolyated fatty acid esters of sorbitan) (e.g., polyoxyethylene sorbitan monostearate, monoisostearate and monolaurate), polyethylene oxide condensates of alkyl phenols, cocoamidopropyl betaine, lauramidopropyl betaine, palmityl betaine, glyceryl monooleate, glyceryl monostearate, fatty alcohols (e.g., cetostearyl and cetyl alcohol), medium chain triglycerides, polyethoxylated castor oil, polyethoxylated alkyl ethers (e.g., ethoxylated isostearyl alcohols), polyethylene glycols (Macrogols), polyoxyethylene stearates, anionic and nonionic emulsifying waxes, propylene glycol, and propylene glycol alginates;

absorbents, such as kaolin and bentonite clay;

lubricants, such as talc, calcium stearate, magnesium stearate, solid polyethylene glycols, zinc stearate, sodium stearate, stearic acid, ethyl oleate, and ethyl laurate;

controlled release agents such as cross-linked polyvinyl pyrrolidone (crospovidone);

opacifying agents such as titanium dioxide;

buffering agents, including alkaline buffering agents, such as sodium hydroxide, sodium citrate, magnesium hydroxide, and aluminum hydroxide;

diluents/tableting agents such as dicalcium phosphate;

antioxidants, including (1) water soluble antioxidants, such as ascorbic acid, cysteine hydrochloride, sodium bisulfate, sodium metabisulfite, and sodium sulphite, (2) oil-soluble antioxidants, such as ascorbyl palmitate, butylated hydroxyanisole (BHA), butylated hydroxytoluene (BHT), lecithin, propyl gallate, and alpha-tocopherol; and (3) metal chelating agents, such as citric acid, ethylenediamine tetraacetic acid (EDTA), tartaric acid, and phosphoric acid;

antibacterial and antifungal agents, such as paraben, chlorobutanol, phenol, sorbic acid;

as well as other non-toxic compatible substances employed in pharmaceutical formulations, such as cyclodextrins, liposomes, and micelle forming agents including mixtures thereof.

Preferred rapidly infusing compositions are those which contain less than 1 wt. preferably less than 0.5 wt. %, preferably less than 0.1 wt. %, preferably less than 0.05 wt. %, preferably less than 0.001 wt. %, preferably 0 wt. %, of other pharmaceutically acceptable carriers and/or excipients, such as those listed above, in particular alkaline buffering agents and/or surfactants.

Also preferred are rapidly infusing compositions which do not contain inert diluents, aqueous carriers, or non-aqueous carriers commonly used in the art for manufacture of liquid dosage forms for oral administration, such as emulsions, microemulsions, solutions, suspensions, syrups, and elixirs. Examples of inert diluents, aqueous or non-aqueous carriers, etc. which are preferably excluded herein may include, but are not limited to, water or other solvents, solubilizing agents, and emulsifiers, such as ethyl alcohol, isopropyl alcohol, ethyl carbonate, ethyl acetate, benzyl alcohol, benzyl benzoate, glycerol, polyethylene glycol, propylene glycol, 1,3-butylene glycol, oils (whether synthetic, semi-synthetic, or naturally occurring, such as long chain triglycerides, mixed glycerides, and free fatty acids, in particular, cottonseed oil, groundnut oil, corn oil, germ, olive oil, castor oil, sesame oil, borage oil, coconut oil, soybean oil, safflower oil, sunflower oil, palm oil, peanut oil, peppermint oil, poppy seed oil, canola oil, hydrogenated soybean oil, hydrogenated vegetable oils, glyceryl distearate, behenic acid, caprylyic/capric glycerides, lauric acid, linoleic acid, linolenic acid, myristic acid, palmitic acid, palmitoleic acid, palmitostearic acid, ricinoleic acid, stearic acid, soy fatty acids, oleic acid, glyceryl esters of fatty acids such as glyceryl behenate, glyceryl isostearate, glyceryl laurate, glyceryl palmitate, glyceryl palmitostearate, glyceryl ricinoleate, glyceryl oleate, glyceryl stearate), tetrahydrofuryl alcohol, fatty acid esters of sorbitan, organic esters such as ethyl oleate, and mixtures thereof, with specific mention being made to ethyl alcohol and sesame oil.

Active Therapeutic Ingredient (ATI)

The amount of active therapeutic ingredient (ATI) which can be combined with the pharmaceutically acceptable carrier and/or excipient system to produce the rapidly infusing composition may vary depending upon the subject being treated, and other factors. The amount of ATI which can be combined with the pharmaceutically acceptable carrier and/or excipient system to produce a single dosage form will generally be that amount which produces a therapeutic effect. Generally, this amount will range from 0.1 to 90 wt. % of ATI, for example, at least 20 wt. %, preferably at least 22 wt. %, preferably at least 24 wt. %, preferably at least 26 wt. %, preferably at least 28 wt. %, preferably at least 30 wt. %, preferably at least 32 wt. %, preferably at least 34 wt. %, preferably at least 36 wt. %, preferably at least 38 wt. %, preferably at least 40 wt. %, preferably at least 42 wt. %, preferably at least 44 wt. %, preferably at least 46 wt. %, preferably at least 48 wt. %, preferably at least 50 wt. %, preferably at least 52 wt. %, preferably at least 54 wt. %, and up to 70 wt. %, preferably up to 68 wt. %, preferably up to 66 wt. %, preferably up to 64 wt. %, preferably up to 62 wt. %, preferably up to 60 wt. %, preferably up to 58 wt. %, preferably up to 56 wt. % of the ATI, based on a total weight of the rapidly infusing composition on a dry basis.

In terms of unit dose, the rapidly infusing composition is generally formulated with 2 to 100 mg of ATI per unit (e.g., tablet), for example at least 2 mg, preferably at least 4 mg, preferably at least 6 mg, preferably at least 8 mg, preferably at least 10 mg, preferably at least 12 mg, preferably at least 14 mg, preferably at least 16 mg, preferably at least 18 mg, preferably at least 20 mg, preferably at least 22 mg, preferably at least 24 mg, and up to 100 mg, preferably up to 75 mg, preferably up to 65 mg, preferably up to 60 mg, preferably up to 55 mg, preferably up to 50 mg, preferably up to 45 mg, preferably up to 40 mg, preferably up to 35 mg, preferably up to 30 mg, preferably up to 25 mg of ATI per unit (e.g., tablet).

In some embodiments, the ATI may be cannabidiol (CBD) or a derivative/analog thereof, sildenafil (VIAGRA), nicotine, morphine, clonazepam, alprazolam, buprenorphine, diazepam, a vitamin, or a mineral.

In preferred embodiments, the rapidly infusing composition is formulated with, as the active therapeutic ingredient, cannabidiol (CBD), or any pharmaceutically acceptable derivative/analog, salt, solvate, or stereoisomer thereof. In some preferred embodiments, CBD or a derivative/analog is the only active therapeutic ingredient in the rapidly infusing composition. In some preferred embodiments, CBD is the only active therapeutic ingredient in the rapidly infusing composition. In some preferred embodiments, a CBD derivative/analog is the only active therapeutic ingredient in the rapidly infusing composition. In other embodiments, CBD may be combined with other active therapeutic ingredients. For example, CBD, formulated as described below may be combined with a water-soluble ATI such as melatonin, as a sleep aid.

Preferred rapidly infusing compositions are those which are formulated with CBD, preferably a solid form of CBD. That is, the rapidly infusing composition is prepared through lyophilization from a drug product suspension in which the CBD is in the form of a solid. In particular, micronized particles of CBD are preferred. In some embodiments, the rapidly infusing composition is formulated with solid CBD in the form of micronized particles having a D50 particle size in the range of 1 µm to 50 µm, for example, those having a D50 particle size of at least 1 µm, preferably at least 10 µm, preferably at least 20 µm, preferably at least 30 µm, preferably at least 40 µm, and up to 50 µm, preferably up to 40 µm, preferably up to 30 µm, preferably up to 20 µm, preferably up to 10 µm.

Even more preferred are those rapidly infusing compositions which are formulated with a solid form of CBD having a purity of at least 95 wt. %, preferably at least 96 wt. %, preferably at least 97 wt. %, preferably at least 98 wt. %, preferably at least 99 wt. %. While CBD having a purity of 100 wt. % is likely not achievable, preferably rapidly infusing compositions are formulated with a solid form of CBD having a purity up to 99.1 wt. %, preferably up to 99.2 wt. %, preferably up to 99.3 wt. %, preferably up to 99.4 wt. %, preferably up to 99.5 wt. %, preferably up to 99.6 wt. %, preferably up to 99.7 wt. %, preferably up to 99.8 wt %, preferably up to 99.9 wt. %. The percent purity of CBD refers to the percent of CBD by mass relative to a total weight of CBD containing material—the CBD containing material being the sum of CBD plus any additional impurities which may be present, such as those impurities originating from the biomass from which the CBD is obtained (e.g., *Cannabis sativa* L./"Industrial Hemp") or encountered during manufacture. The purity may be determined by methods known to those of ordinary skill in the art, for example, one or more of liquid chromatography such as high performance liquid chromatography (HPLC), liquid chromatography-mass spectrometry (LCMS), and liquid chromatography with tandem mass spectrometry (LCMSMS); gas chromatography such as headspace gas chromatography with flame ionization detection (HS-GC-FID), gas chromatography mass spectrometry (GC/MS), and headspace gas chromatography-mass spectrometry (HSGCMS); inductively coupled plasma-mass spectrometry (ICP-MS); and polymerase chain reaction (PCR).

Examples of potential impurities, such as those originating from the biomass from which the CBD is obtained (e.g., *Cannabis sativa* L./"Industrial Hemp") or encountered during manufacture, include, but are not limited to, cannabinoids (other than CBD) including, but not limited to, cannabidivarin (CBDV), cannabichromene (CBC), cannabidiolic acid (CBDa), cannabigerol (CBG), cannabigerolic acid (CBGa), cannabinol (CBN), tetrahydrocannabinolic acid (THCa), tetrahydrocannabivarin (THCV), tetrahydrocannabivarin acid (THCVa), and tetrahydrocannabinol (Δ9-THC) and related THC-cannabinoids such as Δ8-THC;

pesticides including, but not limited to, aldicarb, carbofuran, chlordane, chlorfenapyr, chlorpyrifos, coumaphos, daminozide, dichlorvos (DDVP), dimethoate, ethoprophos, etofenprox, fenoxycarb, fipronil, imazalil, methiocarb, methyl parathion, paclobutrazol, propoxur, spiroxamine, and thiacloprid;

residual solvents including, but not limited to, 1,4-dioxane, 2-butanol, 2-ethoxyethanol, 1,2-dichloroethane, acetone, acetonitrile, benzene, butane, cumene, cyclohexane, chloroform, ethanol, ethyl acetate, ethyl benzene, ethylene oxide, ethylene glycol, ethyl ether, heptane, isopropanol, methanol, methylene chloride, hexanes, isopropyl acetate, pentanes, propane, toluene, tetrahydrofuran, trichloroethene, and xylenes;

microbials including, but not limited to, *Aspergillus flavus, Aspergillus fumigatus, Aspergillus niger, Aspergillus terreus, Salmonella*, and Shiga toxin-producing *E. coli;* mycotoxins including, but not limited to, aflatoxins (e.g., aflatoxin B1, aflatoxin B2, aflatoxin G1, and aflatoxin G2) and ochratoxin A;

heavy metals including, but not limited to, arsenic, cadmium, lead, and mercury;

terpenes including, but not limited to, (1) monoterpenes such as camphene, camphor, 3-carene, α-cedrene, cedrol, endo-fenchyl alcohol, eucalyptol, fenchone, geraniol, geranul acetate, hexahydrothymol, isoborneol, isopulegol, limonene, linalool, p-mentha-1,5-diene, β-myrcene, α- and β-pinene, pulegone, sabinene and hydrate, α- and γ-terpinene, terpineol, terpinolene, α-, β-, and γ-terpineol, nerol, borneol, and ocimene isomers I and II, and (2) sesquiterpenes such as α-bisabolol, β-caryophyllene, caryophyllene oxide, guaiol, α-humulene, cis- and trans-nerolidol, and valencene; as well as mixtures thereof.

In some embodiments, the rapidly infusing composition is formulated with a form of CBD which contains less than 1 wt. %, preferably less than 0.5 wt. %, preferably less than 0.1 wt. %, preferably less than 0.05 wt. %, preferably less than 0.001 wt. %, preferably 0 wt. % of the above listed impurities, based on a total weight of the CBD material, with specific mention being made to THC. In some embodiments, the rapidly infusing composition is formulated with a form of CBD which contains no impurity, such as those listed above, in an amount above the limits of detection (LOD) and/or limits of quantification (LOQ) for the technique/instrumentation being used to make such a determination. For example, preferred rapidly infusing compositions are those formulated with a pure form of CBD which has a THC content of less than 0.1577 wt. %, preferably less than 0.1 wt. %, preferably less than 0.01 wt. %, preferably less than 0.001 wt. %, based on a total weight of the CBD material. In preferred embodiments, the rapidly infusing composition is formulated with a pure form of CBD which consists of, or consists essentially of, CBD.

The full effects of the present disclosure may not be realized when the rapidly infusing composition is formulated with an impure form of CBD or when the rapidly infusing composition is formulated with CBD in oil/liquid form. Without being bound by theory, it is believed that during the manufacture of the rapidly infusing composition, when the CBD is in solid form with sufficiently high purity, lyophilization from a drug product suspension generates a structured and robust matrix of gelatin as the water is removed via sublimation, and an even distribution of the CBD throughout the gelatin matrix. Such a structured assembly of CBD suspended within a gelatin matrix is believed to afford the rapidly infusing composition with rapid disintegration properties and efficient transfer of CBD from the hydrophilic vehicle to the mucous membrane of the buccal cavity, or the ventral surface under the tongue, upon administration.

On the contrary, when the rapidly infusing composition is formulated with an impure (oil) form of CBD during manufacture, lyophilization is instead performed from an o/w emulsion of CBD, which may produce an unstable, disordered matrix of gelatin more prone to collapse back into an oil or semi-solid state. The resulting rapidly infusing composition tends to suffer from poor shelf-life, increased disintegration times, and inferior delivery/uptake of the CBD into systemic circulation reflected in longer onset times and overall less efficacy against pain indications.

Accordingly, any CBD manufacturing method known by those of ordinary skill in the art which provides CBD in solid form, and of sufficient purity, may be utilized herein for preparation of the CBD ATI. For illustration purposes, one exemplary CBD manufacturing method is described below, although it should be understood that numerous modifications and variations are possible, and the CBD may be produced using methods or techniques otherwise than as specifically described.

CBD may be extracted/isolated from biomass, for example, a cured flower of *Cannabis sativa* L. The biomass may contain, for example, at least 1 mg/g, preferably at least 2 mg/g, preferably at least 3 mg/g, and up to 10 mg/g, preferably up to 8 mg/g, preferably up to 6 mg/g, preferably up to 4 mg/g of CBD; at least 50 mg/g, preferably at least 60 mg/g, preferably at least 70 mg/g, preferably at least 80 mg/g, preferably at least 90 mg/g, and up to 150 mg/g, preferably up to 140 mg/g, preferably up to 130 mg/g, preferably up to 120 mg/g, preferably up to 110 mg/g, preferably up to 100 mg/g of cannabidiolic acid (CBDa); and no detectable amount of THC. Extraction of the biomass with an alcoholic solvent (e.g., ethanol) and cooling may form a tincture. The tincture may be filtered to remove sediment and particulates, and concentrated, for example, using a rotary evaporator.

An aluminum phyllosilicate clay (e.g., bentonite) may then be mixed with the concentrated product at a weight ratio of at least 2:1, preferably at least 3:1, preferably at least 4:1, and up to 6:1, preferably up to 5:1, and the resulting mix filtered to remove fats, waxes, and lipids. The product may then be frozen/winterized, after which the frozen product may be again filtered and taken through another solvent removal/recovery cycle to form a winterized crude.

Decarboxylation of the winterized crude by heating, for example in an induction oven centrifugal reactor, may be performed to remove the carboxylic acid functionality from the cannabinoids. Distillation of the decarboxylated material may then provide a distillate.

The distillate may then be precipitated in a high-pressure reactor using an alkane solvent (e.g., pentane), and a cryo-chamber may be used to subject the precipitate to cryo temperatures (e.g., −20° F. to −40° F.) to promote the growth of crystalline CBD. The CBD crystals may be washed with an alkane solvent (e.g., pentane), filtered, and ground to a finer particle size, prior to being purged in a vacuum oven for removal of solvents and impurities. The obtained solid CBD may then be analyzed for purity, as appropriate.

Methods to be used for preparing the rapidly infusing composition are preferably pharmaceutical-GMP compliant, and may include generally bringing into association the ATI (e.g., CBD) with the gelatin and sugar alcohol (e.g., mannitol), and, optionally, one or more accessory pharmaceutically acceptable carrier and/or excipient ingredients, in water to form a drug product suspension which is then lyophilized.

One exemplary method for manufacturing a drug product container assembly in which the therapeutic product is in the form of a rapidly infusing composition is presented below, although it should be understood that numerous modifications and variations are possible, and the rapidly infusing composition may be produced using methods or techniques otherwise than as specifically described.

Purified water, gelatin, and sugar alcohol (e.g., mannitol) may be charged to a mixer, for example a pot equipped with an overhead stirrer, and heated (e.g., 40 to 80° C.) with agitation until complete solvation. Any desired sweetener (e.g., a mixture of sucralose and acesulfame-K) may then be added and allowed to dissolve.

Upon cooling, for example to 20 to 35° C., the solution may next be transferred to a homogenizer, and the ATI (e.g., CBD) may be subsequently charged and dispersed using the homogenizer, with preferable micronization of the ATI, to form a drug product suspension. Any desired flavorant and colorant may be added at this point with continued mixing. The drug product suspension may be transferred to a second mixer whilst maintaining a cooled temperature (e.g., 20 to 35° C.).

In a blistering machine equipped with a dosing system, a well layer having blister pockets (i.e. a blister tray) may next be filled with the drug product suspension until achieving a target dose weight, followed by freezing in a suitable cryochamber. The well layer may be transferred from the cryochamber to a suitable refrigerated storage cabinet (e.g., at a temperature below 0° C.) to keep the product frozen prior to lyophilization. Then, the frozen well layer may be loaded into a lyophilizer and subject to lyophilization to sublimate the water and form the rapidly infusing compositions. Finally, when the lyophilization cycle is deemed complete, final sealing (e.g., heat sealing of the lidding layer) may be performed to provide the rapidly infusing compositions in single dose units in individual blister pockets.

In preferred embodiments, the rapidly infusing composition comprises, consists essentially of, or consists of gelatin, mannitol, sweetener, flavorant, colorant, and as the ATI, CBD.

Also contemplated for use as an active therapeutic ingredient are derivatives/analogs of CBD that retain the desired activity for the treatment of pain. Derivatives/analogs that retain substantially the same activity as CBD, or more preferably exhibit improved activity, may be produced according to standard principles of medicinal chemistry, which are well known in the art. Such derivatives/analogs may exhibit a lesser degree of activity than CBD, so long as they retain sufficient activity to be therapeutically effective. Derivatives/analogs may exhibit improvements in other properties that are desirable in active therapeutic agents such as, for example, improved solubility, reduced toxicity, enhanced uptake, increased bioavailability, etc. Contemplated CBD derivatives/analogs include, but are not limited to, cannabidiolic acid compounds and variants thereof, such as cannabidiolic acid and esters of cannabidiolic acid, in particular alkyl esters of cannabidiolic acid (e.g., cannabidiolic acid methyl ester); 5' side chain modified CBD compounds such as cannabidivarin (CBDV), cannabidiol-dimethylheptyl (CBD-DMH), and 1,2-cannabidiol-dimethylheptyl (1,2-CBD-DMH); 7-methyl modified CBD compounds such as 7-carboxy cannabidiol (7-COOH-CBD) and 7-hydroxy cannabidiol (7-OH-CBD); hydrogenated CBD compounds such as 8,9-dihydrocannabidiol ($H_2$-CBD) and tetrahydrocannabidiol ($H_4$-CBD); halogenated CBD compounds such as 3'-chloro-CBD, 3',5'-dichloro-CBD, 3'-bromo-CBD, 3',5'-dibromo-CBD, 3'-iodo-CBD, and 3',5'-diiodo-CBD; hydroxyl group modified CBD compounds such as desoxy-CBD and dimethylether CBD; cannabielsoin (CBE); machaeridiols A, B, and C; as well as any pharmaceutically acceptable salts, solvates, and/or stereoisomers of such compounds. When a CBD derivative/analog is used as the ATI in the disclosed rapidly infusing composition, particular preference is given to cannabidiolic acid methyl ester.

It is contemplated that CBD or derivatives/analogs of CBD may be useful in combination. It is also contemplated that CBD or derivatives/analogs of CBD may be useful in combination with current Standards of Care for the treatment of pain as well as any that evolve over the foreseeable future. Specific dosages and dosing regimens would be based on physicians' evolving knowledge and the general skill in the art.

The examples below are intended to further illustrate the materials and methods of the present disclosure, and are not intended to limit the scope of the claims.

Where a numerical limit or range is stated herein, the endpoints are included. Also, all values and subranges within a numerical limit or range are specifically included as if explicitly written out.

As used herein the words "a" and "an" and the like carry the meaning of "one or more."

The present disclosure also contemplates other embodiments "comprising", "consisting of" and "consisting essentially of", the embodiments or elements presented herein, whether explicitly set forth or not.

All patents and other references mentioned above are incorporated in full herein by this reference, the same as if set forth at length.

Obviously, numerous modifications and variations of the present invention are possible in light of the above teachings. It is therefore to be understood that, within the scope of the appended claims, the invention may be practiced otherwise than as specifically described herein.

EXAMPLES

Drug Product Container Assembly
Ingredients

The ingredients that were used to make the rapidly infusing composition and the container are given in Table 1. USP=United States Pharmacopeia. EP=European Pharmacopoeia. NF=National Formulary.

TABLE 1

| Ingredients | | |
|---|---|---|
| Ingredient | Primary Function | Specification |
| Gelatin | Matrix former | USP/EP/NF |
| Mannitol | Bulking agent | USP/EP |
| Lemon-lime flavor powder | Flavorant | Non-compendial |

TABLE 1-continued

Ingredients

| Ingredient | Primary Function | Specification |
|---|---|---|
| CBD isolate | ATI | Non-compendial |
| Sucralose | Sweetener | USP/NF |
| Acesulfame-K | Sweetener | USP/NF |
| FD&C Yellow #5 | Colorant | Non-compendial |
| Purified water | Vehicle | USP/EP |
| Lidding material | Packaging | Non-compendial |
| Well material | Packaging | Non-compendial |

An example rapidly infusing composition was made using the formulation given in Table 2. The amount of each component is expressed in terms of weight percentage relative to a total weight (100%). The weight percentage of each component in the drug product suspension is on a wet basis (prior to removal of water). The weight percentage of each component in the rapidly infusing composition is on a dry basis (after removal of water) (see also U.S. Provisional Application 63/114,194 and U.S. patent application Ser. No. 17/225,738—each incorporated herein by reference in its entirety).

TABLE 2

Example rapidly infusing composition

| Ingredient | Drug product suspension % wt./wt. (wet) | Rapidly infusing composition wt./unit (dry) | Rapidly infusing composition % wt./wt. (dry) |
|---|---|---|---|
| Gelatin | 3.5 | 10.5 mg | 22.7 |
| Mannitol | 3.0 | 9 mg | 19.4 |
| Lemon-lime flavor powder | 0.2 | 0.6 mg | 1.3 |
| CBD isolate | 8.4 | 25 mg | 54.0 |
| Sucralose | 0.2 | 0.6 mg | 1.3 |
| Acesulfame-K | 0.2 | 0.6 mg | 1.3 |
| FD&C Yellow #5 | Trace | Trace | Trace |
| Purified water | 84.5 | Removed during manufacture | Removed during manufacture |
| Total | 100.0 | — | 100.0 |

Methods of Making the Drug Product Container Assembly

Purified water was charged to a pot and mixed using an overhead stirrer as an agitating device.

With agitation, the requisite amount of gelatin and mannitol were dispersed, and the mixture was heated until the excipients were dissolved.

Once dissolved, the sweeteners sucralose and acesulfame-K were added and allowed to dissolve.

The solution was cooled to 30° C., moved to an overhead homogenizer, and then the requisite amount of cannabidiol (CBD) isolate was charged and dispersed using the homogenizer to micronize the CBD and create a drug product suspension.

The requisite amount of Lemon-Lime flavor was charged and mixed for 10 minutes, then the FD&C Yellow #5 colorant was added.

The resulting drug product suspension was transferred to a second overhead mixer and maintained at a temperature of 30° C. for the ensuing dosing operation.

In a blistering machine equipped with a dosing system, blister pockets of a well layer were filled with a target dose weight of 300.0 mg of the drug product suspension.

The product was frozen in a suitable cryochamber and then the well layers were transferred from the cryochamber to a suitable refrigerated storage cabinet (temperature below 0° C.) prior to lyophilization to keep the product frozen.

The frozen well layers were loaded from the refrigerated storage cabinet into lyophilizers and the product was lyophilized (water was sublimated) to form the rapidly infusing compositions.

When the lyophilization cycle was completed, the rapidly infusing compositions were transferred from the lyophilizers to the blistering machine where the well layers were each heat sealed with a lidding layer. The resulting tablets are flat-topped circular units approximately 15 mm in diameter with a convex bottom packaged in individual pockets of the container.

The following tests were performed:
A seal integrity test was performed at −0.5 Bar for 30 seconds, 1-minute soak time
Visual inspection was performed
Dry weight testing was performed

The invention claimed is:

1. A container for a therapeutic product, comprising:
a substantially planar lidding layer, and
a well layer,
wherein the lidding layer comprises, in order from an exterior lid side to an interior lid side:
a labeling layer;
a thermoplastic polymer lidding layer; and
an aluminum lidding layer:
wherein the interior lid side is removably attached to an interior well side,
wherein the well layer is shaped to form one or more pockets between the interior lid side and the interior well side, each pocket configured to enclose the therapeutic product,
wherein the one or more pockets each comprise a substantially flat portion in the center of the pocket and the substantially flat portion of the one or more pockets is connected to the top of the pocket by a sidewall comprising two or more sections, wherein a lower section of the sidewall exhibits a greater degree of concavity than an upper section of the sidewall, and
wherein the well layer comprises, in order from the interior well side to an exterior well side:
a first thermoplastic polymer well layer;
a first polyamide layer;
an aluminum well layer;
a second polyamide layer; and
a second thermoplastic polymer well layer.

2. The container of claim 1, wherein the lidding layer and/or the well layer further comprise adhesive interlayers.

3. The container of claim 1, wherein the lidding layer and the well layer each independently have:
a moisture vapor transmission rate of less than 0.05 g/m$^2$/day measured at 38° C. and 90% relative humidity, and/or
an oxygen transmission rate of less than 0.01 mL/m$^2$/day measured at 23° C. and 50% relative humidity.

4. The container of claim 1, wherein the lidding layer further comprises a lacquer layer at the interior lid side.

5. The container of claim 1, wherein the thermoplastic polymer lidding layer, the first thermoplastic polymer well layer, and the second thermoplastic polymer well layer each independently comprise at least one polymer selected from the group consisting of polyvinylchloride, polyethylene terephthalate, polyamide, polyethylene, poly(lactic-co-glycolic acid), polytetrafluoroethylene, polyvinylidene fluoride, polylactic acid, polypropylene, polystyrene, polyvinyl acetate, and polyvinylidene chloride.

6. The container of claim 5, wherein the first and second thermoplastic polymer well layers consist essentially of polyvinylchloride.

7. The container of claim 1, wherein the first and second polyamide layers comprise oriented polyamide.

8. The container of claim 1, wherein the labeling layer comprises paper.

9. The container of claim 1, wherein the lidding layer has an average layer thickness in a range of 90-130 μm, and
wherein the well layer has an average layer thickness in a range of 190-300 μm.

10. The container of claim 1, having one or more edges or corners where the lidding layer and the well layer are not attached to each other.

11. The container of claim 1, wherein the one or more pockets includes at least two pockets, and
wherein the lidding layer and the well layer have a perforated line between the at least two pockets.

12. The container of claim 1, wherein the one or more pockets includes at least three pockets separated by at least two perforated lines, and
wherein each adjacent two perforations are spaced by a distance in a range of 20-50 mm.

13. The container of claim 1, wherein the lidding layer and/or the well layer are knurled where the interior lid side is removably attached to the interior well side of the well layer.

14. The container of claim 1, wherein the one or more pockets are each rotationally symmetric about a central axis and have a non-convex cross-sectional profile.

15. The container of claim 1, wherein the substantially flat portion in the center of the pocket includes a raised or lowered portion(s) to deboss or emboss a logo or other information into the therapeutic product.

16. The container of claim 1, wherein the one or more pockets each has a volume in a range of 0.3-4.0 cm$^3$.

17. The container of claim 1, wherein the one or more pockets each has a vertical depth in a range of 3-10 mm.

18. The container of claim 1, wherein the lower section of the sidewall and the upper section of the sidewall each comprises a plurality of planar faces.

19. The container of claim 18, wherein the substantially flat portion in the center of the pocket is octagonal in shape.

20. A drug product container assembly, comprising:
the container of claim 1, and
at least one therapeutic product in the at least one pocket, wherein the at least one therapeutic product is a rapidly infusing composition.

21. The drug product container assembly of claim 20, wherein the rapidly infusing composition has a disintegration time of approximately 1 to 30 seconds in deionized water maintained at 37° C.±2° C.

22. The drug product container assembly of claim 20, wherein the rapidly infusing composition has a disintegration time of approximately 1 to 5 seconds in deionized water maintained at 37° C.±2° C.

23. The drug product container assembly of claim 20, wherein the rapidly infusing composition comprises a pharmaceutically acceptable binder and/or excipient system comprising gelatin and a sugar alcohol.

24. The drug product container assembly of claim 23, wherein the sugar alcohol comprises mannitol.

25. The drug product container assembly of claim 20, wherein the rapidly infusing composition is lyophilized.

26. The drug product container assembly of claim 20, wherein the rapidly infusing composition comprises a therapeutically effective amount of cannabidiol or a derivative/analog thereof.

27. The drug product container assembly of claim 26, wherein the rapidly infusing composition comprises a therapeutically effective amount of cannabidiol.

28. The drug product container assembly of claim 25, wherein the rapidly infusing composition comprises a therapeutically effective amount of a derivative/analog of cannabidiol.

29. The drug product container assembly of claim 27 wherein the derivative/analog of cannabidiol is cannabidiolic acid methyl ester.

30. The container of claim 15, wherein the substantially flat portion in the center of the pocket comprises a raised portion forming an identifiable feature.

31. The container of claim 15, wherein the substantially flat portion in the center of the pocket comprises a depressed portion forming an identifiable feature.

\* \* \* \* \*